US011224419B2

(12) United States Patent
Perkins et al.

(10) Patent No.: US 11,224,419 B2
(45) Date of Patent: Jan. 18, 2022

(54) BI-DIRECTIONAL BARBED SUTURE WITH TAILORED SUTURE SEGMENTS

(71) Applicant: ETHICON LLC, San Lorenzo, PR (US)

(72) Inventors: Jason T. Perkins, Somerville, NJ (US); Jason Huff, Collingswood, NJ (US); John A. Killion, Somerville, NJ (US)

(73) Assignee: CILAG GMBH INTERNATIONAL, Zug (CH)

( * ) Notice: Subject to any disclaimer, the term of this patent is extended or adjusted under 35 U.S.C. 154(b) by 212 days.

(21) Appl. No.: 16/455,952

(22) Filed: Jun. 28, 2019

(65) Prior Publication Data

US 2020/0405300 A1    Dec. 31, 2020

(51) Int. Cl.
*A61B 17/06* (2006.01)
(52) U.S. Cl.
CPC ............. *A61B 17/06166* (2013.01); *A61B 2017/0619* (2013.01); *A61B 2017/06057* (2013.01); *A61B 2017/06176* (2013.01)
(58) Field of Classification Search
CPC .... A61B 17/06166; A61B 2017/06057; A61B 2017/06176; A61B 2017/0619; A61B 90/92; A61B 17/0487; A61B 2017/00477; A61B 2017/0472; A61B 2017/00004; A61B 2017/0608; A61B 2017/06085; A61B 2017/00526; A61L 17/12; A61L 17/105; A61L 17/00
See application file for complete search history.

(56) References Cited

U.S. PATENT DOCUMENTS 5,383,904 A * 1/1995 Totakura ............... A61B 17/06
606/228
5,645,568 A * 7/1997 Chervitz .......... A61B 17/06166
606/228
(Continued)

FOREIGN PATENT DOCUMENTS

EP    2446832 A1    5/2012
EP    2759266 A2    7/2014
(Continued)

OTHER PUBLICATIONS

U.S. Appl. No. 11,103,230, filed Aug. 2021, Kim; Young Jae.*
(Continued)

*Primary Examiner* — Julian W Woo

(57) ABSTRACT

A wound closure device can be provided as described herein. In an example, the wound closure device includes a first suture segment having a first suture configuration and a second suture segment having a second suture configuration. The first and second suture configurations can be different from each other. For example, the first suture configuration can includes a first set of characteristics such as barbed or non-barbed, barb sizes, filament sizes, colors, materials, and/or the like and the second suture configuration can include a second set of characteristics such as barbed or non-barbed, barb sizes, filament sizes, colors, materials and/or the like that can be different from the first set of characteristics. The wound closure device can further include connecting section configured to provide a transition from the first suture segment to the second suture segment.

48 Claims, 11 Drawing Sheets

(56) References Cited

U.S. PATENT DOCUMENTS

| | | | |
|---|---|---|---|
| 5,865,836 | A | 2/1999 | Miller |
| 6,783,524 | B2 | 8/2004 | Anderson et al. |
| 6,848,152 | B2 | 2/2005 | Genova et al. |
| 7,850,894 | B2 | 12/2010 | Lindh, Sr. et al. |
| 8,012,171 | B2 * | 9/2011 | Schmieding ............. D04C 1/06 |
| | | | 606/228 |
| 8,353,931 | B2 | 1/2013 | Stopek et al. |
| 8,721,664 | B2 | 5/2014 | Ruff et al. |
| 8,721,681 | B2 | 5/2014 | Ruff et al. |
| 8,733,223 | B2 | 5/2014 | Lindh, Sr. et al. |
| 8,961,560 | B2 * | 2/2015 | Avelar .................. A61B 90/98 |
| | | | 606/228 |
| 9,044,225 | B1 | 6/2015 | Goraltchouk et al. |
| 9,095,335 | B2 | 8/2015 | Bogart et al. |
| 9,241,709 | B2 | 1/2016 | Marczyk et al. |
| 9,675,341 | B2 * | 6/2017 | D'Agostino ..... A61B 17/06133 |
| 10,729,429 | B2 * | 8/2020 | Cohen .............. A61B 17/06166 |
| 2004/0116963 | A1 | 6/2004 | Lattouf |
| 2005/0267532 | A1 * | 12/2005 | Wu .................. A61B 17/06166 |
| | | | 606/228 |
| 2007/0257395 | A1 | 11/2007 | Lindh |
| 2010/0146770 | A1 | 6/2010 | Morency |
| 2011/0046669 | A1 * | 2/2011 | Goraltchouk .... A61B 17/06166 |
| | | | 606/228 |
| 2011/0125188 | A1 | 5/2011 | Goraltchouk |
| 2011/0264138 | A1 | 10/2011 | Avelar |
| 2011/0282386 | A1 * | 11/2011 | Friedrich ......... A61B 17/06166 |
| | | | 606/228 |
| 2013/0226233 | A1 | 8/2013 | D Agostino et al. |
| 2014/0081321 | A1 | 3/2014 | Nawrocki et al. |
| 2014/0179991 | A1 | 6/2014 | Miller |
| 2014/0257378 | A1 | 9/2014 | Norton et al. |
| 2015/0119933 | A1 * | 4/2015 | Kosa ................. A61B 17/0401 |
| | | | 606/224 |

FOREIGN PATENT DOCUMENTS

| | | |
|---|---|---|
| EP | 2108319 B1 | 11/2016 |
| EP | 3138506 A1 | 3/2017 |
| EP | 3138507 A1 | 3/2017 |
| GB | 1091282 | 7/1964 |
| WO | 2007112024 A3 | 11/2008 |
| WO | 2008/157142 A2 | 12/2008 |

OTHER PUBLICATIONS

U.S. Appl. No. 11,103,232, filed Aug. 2021, Kim; Young Jae.*
International Search Report dated Oct. 12, 2020 for International Appln. No. PCT/IB2020/055543.

* cited by examiner

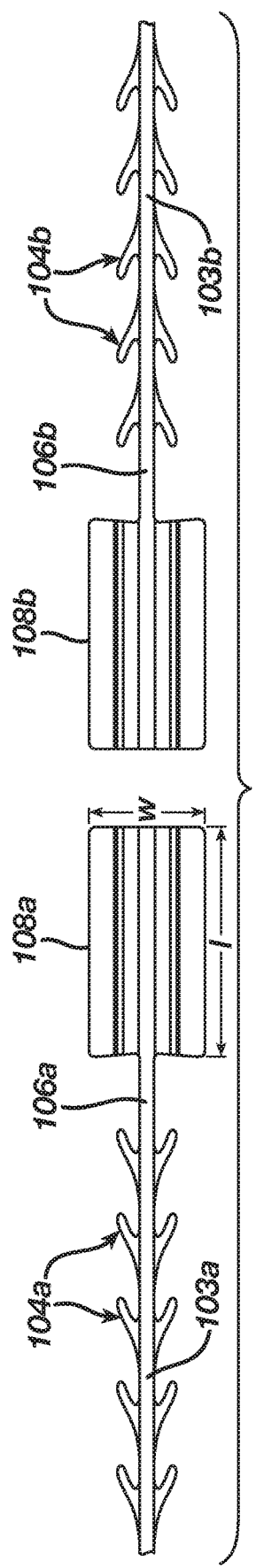
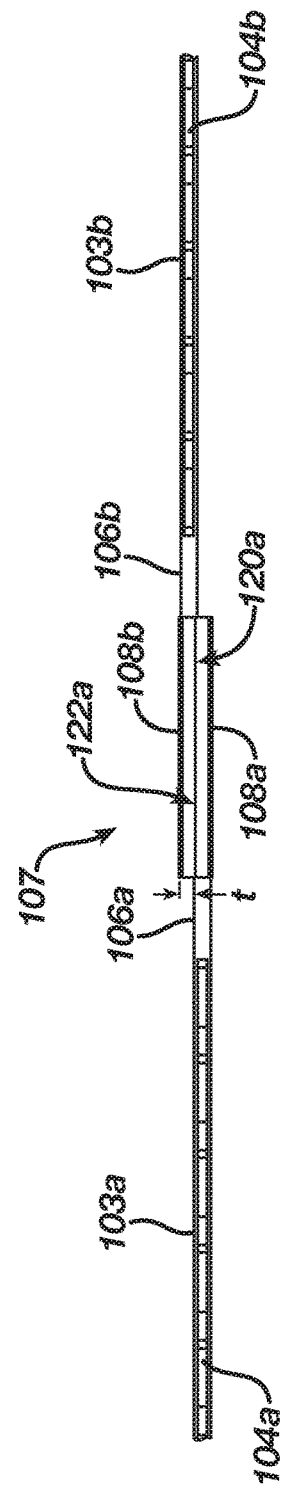
FIG. 3
FIG. 4
FIG. 5A
FIG. 5B

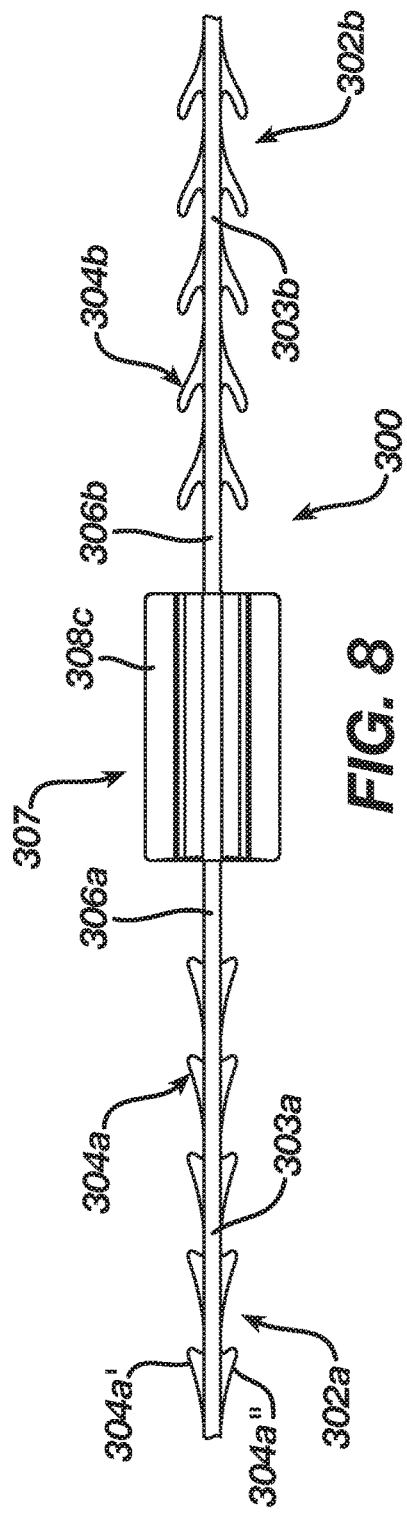
FIG. 8
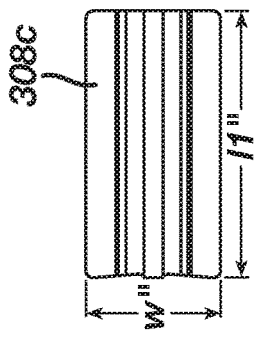
FIG. 9
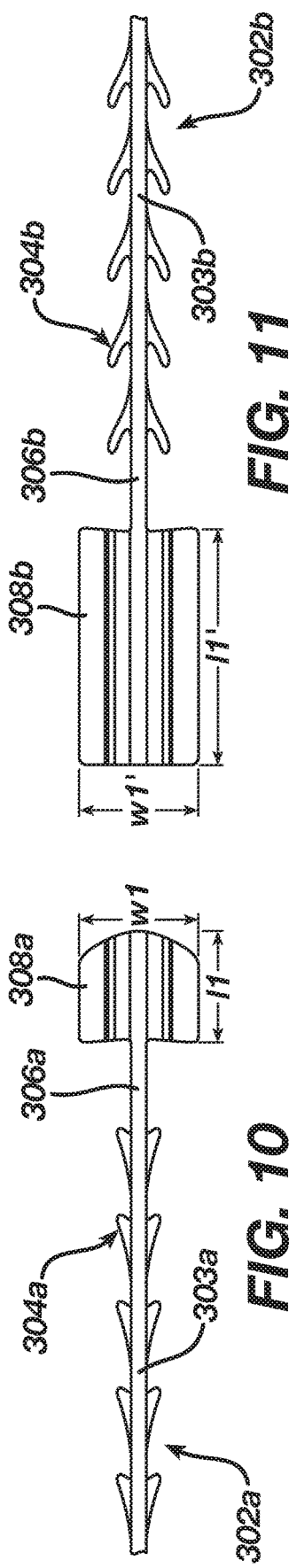
FIG. 10
FIG. 11

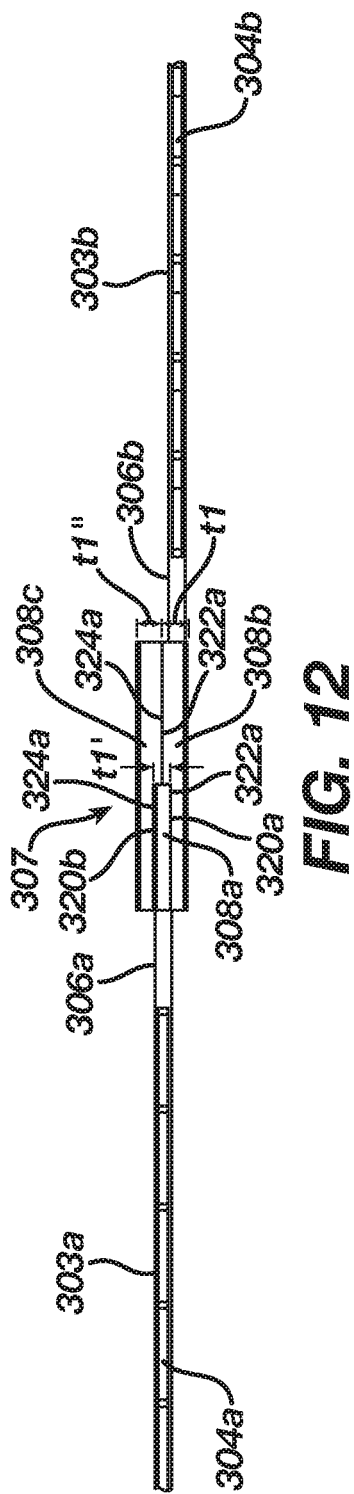
FIG. 12
FIG. 13A
FIG. 13B

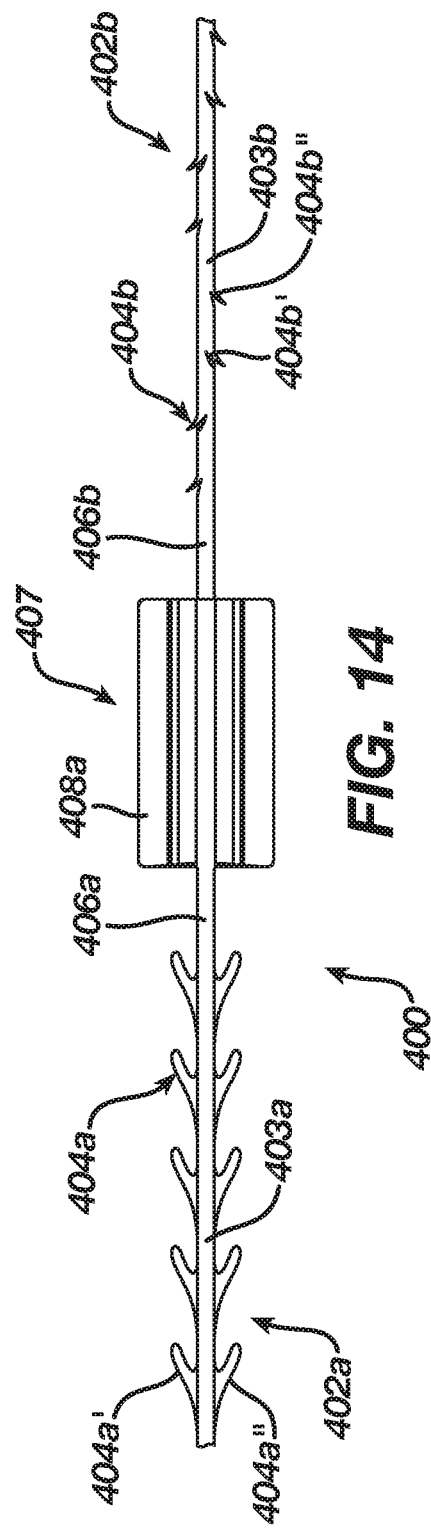
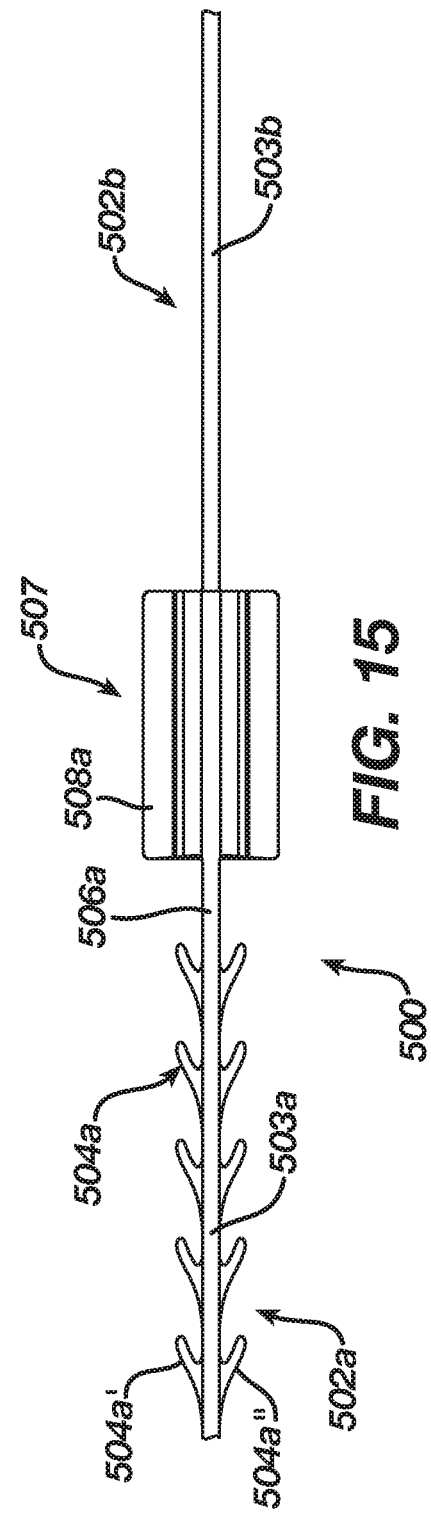
FIG. 14
FIG. 15

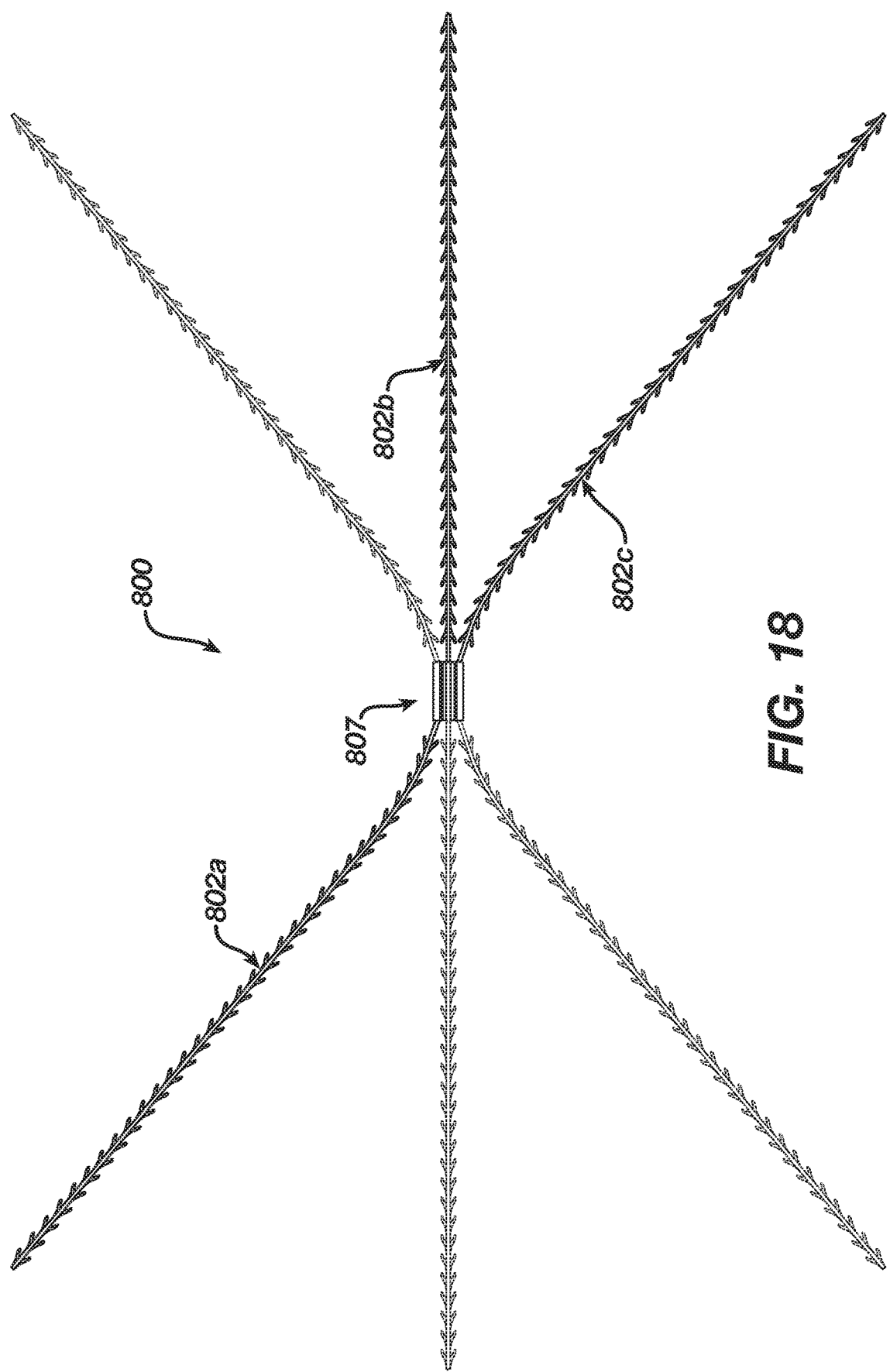

BI-DIRECTIONAL BARBED SUTURE WITH TAILORED SUTURE SEGMENTS

BACKGROUND

Many wounds and surgical incisions are closed using surgical sutures or some other wound closure device. For example, a surgeon can close a wound or surgical incision using a suture, a barbed suture, and/or the like. Often, in a surgical procedure, the surgeon needs to use multiple sutures or wound closure devices to close a wound or surgical incision depending on different tissue layers that are part of the wound or surgical incision. For example, the surgeon may need to select a suture or wound closure device having a first set of properties such as appropriate size, length, material, construction such as being barbed, needle properties, antibacterial properties, and/or the like based on a given tissue layer of the wound or surgical incision being closed and another suture or wound closure device with a different set of properties for another tissue layer of the wound or surgical incision being closed. Unfortunately, having to select and use multiple sutures or wound closure devices during a procedure can increase the time it takes to close the wound or surgical incision thereby increasing the time of the procedure itself, the time the patient is under anesthesia, and/or the like.

SUMMARY

A suture for approximating tissue can be provided. In examples, the suture can comprise multiple suture segments with the same or different configurations of suture segments such that a bi-directional wound closure device for multi-purpose or multi-layer tissue closure can be created. For example, the suture comprises suture segments such as a first suture segment and a second suture segment. The suture segments can be made of a thermoplastic material such as polydioxanone (PDS) in an example. The suture segments can have suture configurations. For example, the first suture segment can have a first suture configuration and the second suture segment can have a second suture configuration. The suture configurations such as the first and second suture configurations can be the same or different. In an example, the suture segments such as the first and second suture segments can be connected to each other by a connecting section or transition zone (e.g., a joining member).

In an example, one or more of the suture segments and configurations thereof can include knotless tissue control devices, or barbed sutures. Typically, barbed sutures are constructed with a series of "barbs," "protrusions," (e.g., used interchangeably herein) that extend outwardly from a filament or filamentary element of the suture (e.g., thereby forming the suture segments). These barbs, or protrusions, function to increase the holding strength of the suture and/or eliminate the need for knot tying. The barbs can be made from a thermoplastic material (e.g., absorbable and/or non-absorbable) such as PDS in an example.

Further, in an example, one or more of the suture segments can include anchors, tabs, and/or the like on an end thereof. The anchors, tabs, and/or the like can provide a "stop" (e.g., a stop element) at the end that can increase the holding strength of the suture and further eliminates the need to tie knots to secure the suture. The anchors, tabs, and/or the like can be made of a thermoplastic material (e.g., absorbable and/or nonabsorbable) such as PDS. Further, the anchors, tabs, and/or the like can provide a transition zone or connecting section between suture segments. For example, each of the anchors, tabs, and/or the like at the end of each of the suture segments (e.g., first and second stop elements at the end of the respective first and second suture segments) can be joined together to form a connecting section or transition zone between suture configurations. According to an example, radiofrequency (RF) energy or another appropriate energy sources, heat sources, and/or the like can be used to join the anchors, tabs, and/or the like together thereby joining the suture segments together and forming the connecting section or transition zone.

As such, according to examples herein, two or more sutures or suture segments or legs (e.g., barbed and/or non-barbed suture segments or legs) of varying materials (e.g., absorbable or nonabsorbable polymers), sizes, lengths, anchor geometries, needles, properties (e.g., anti-bacterial properties), constructions (e.g., monofilament or multi-filament), and/or the like can be joined by a lamination or welding process. In such an example, each resulting segment or leg of the suture can be uniquely tailored with the appropriate set of features needed to perform a particular tissue closure, which may be different for each segment or leg of the device. For example, one segment can include a barbed suture that may be symmetric, made of PDS, undyed and of a particular size (e.g., 3-0) and another segment or leg can include a barbed suture that may be symmetric, made of PDS, dyed, and of the same size (e.g., 3-0). In other examples, one suture segment can include a combination of types (e.g., barbed and/or non-barbed), materials (e.g., absorbable or nonabsorbable polymers), sizes, lengths, anchor geometries, needles, properties (e.g., anti-bacterial properties), constructions (e.g., monofilament or multi-filament), and/or the like.

A wound closure or suture device, as described herein, with multiple suture segments can enable a surgeon to close multiple tissue layers and/or complete multiple jobs at once and with one device. Further, a wound closure or suture device as described herein, can enable multiple surgeons to suture at the same time, which, for example, can increase efficiency and/or reduce an amount of time a patient may be under anesthesia.

Additionally, the example wound closure or suture device described herein can reduce an amount of packaging materials. For example, as described herein, typically multiple wound closure devices can be used to close different tissue layers and each of those devices can be in its own package. In examples herein, the wound closure device that can be tailored to the patient can be packaged together reducing the amount of packaging materials.

Additionally, equipment and tooling can limit a length of a suture segment in a wound closure device. The example wound closure device and method or process of producing the same can enable a longer length of the same or varying suture segments than may be currently available. For example, a lamination process or method as described herein for creating a wound closure device can enable an overall length of the bi-directional strand, or the device, for example, to be up to twice a maximum length of an individual strand without investing in equipment or tooling to produce an integrally-formed bi-directional strand having the same length or features.

BRIEF DESCRIPTION OF THE DRAWINGS

FIG. 3 depicts an exploded view of stop elements of the wound closure device of FIG. 1, for example, prior to forming a connecting section.

FIG. 4 illustrates a top view of the connecting section of the wound closure device of FIG. 1.

FIG. 5A-5B illustrates a cross section of the connecting section of the wound closure device of FIG. 1.

FIG. 8 illustrates another example of a wound closure device and a connecting section thereof according to an example herein.

FIGS. 9-11 depicts an exploded view of stop elements and/or tabs of the wound closure device of FIG. 8, for example, prior to forming the connecting section.

FIG. 12 illustrates a top, perspective view of the connecting section of the wound closure device of FIG. 8.

FIG. 13A-13B illustrates a cross-section of the connecting section of the wound closure device of FIG. 8.

FIG. 14 illustrates another example of a wound closure device and a connecting section thereof according to an example herein.

FIG. 15 illustrates another example of a wound closure device and a connecting section thereof according to an example herein.

FIG. 18 illustrates another example of a wound closure device and a connecting section thereof according to an example herein.

Figure 1:
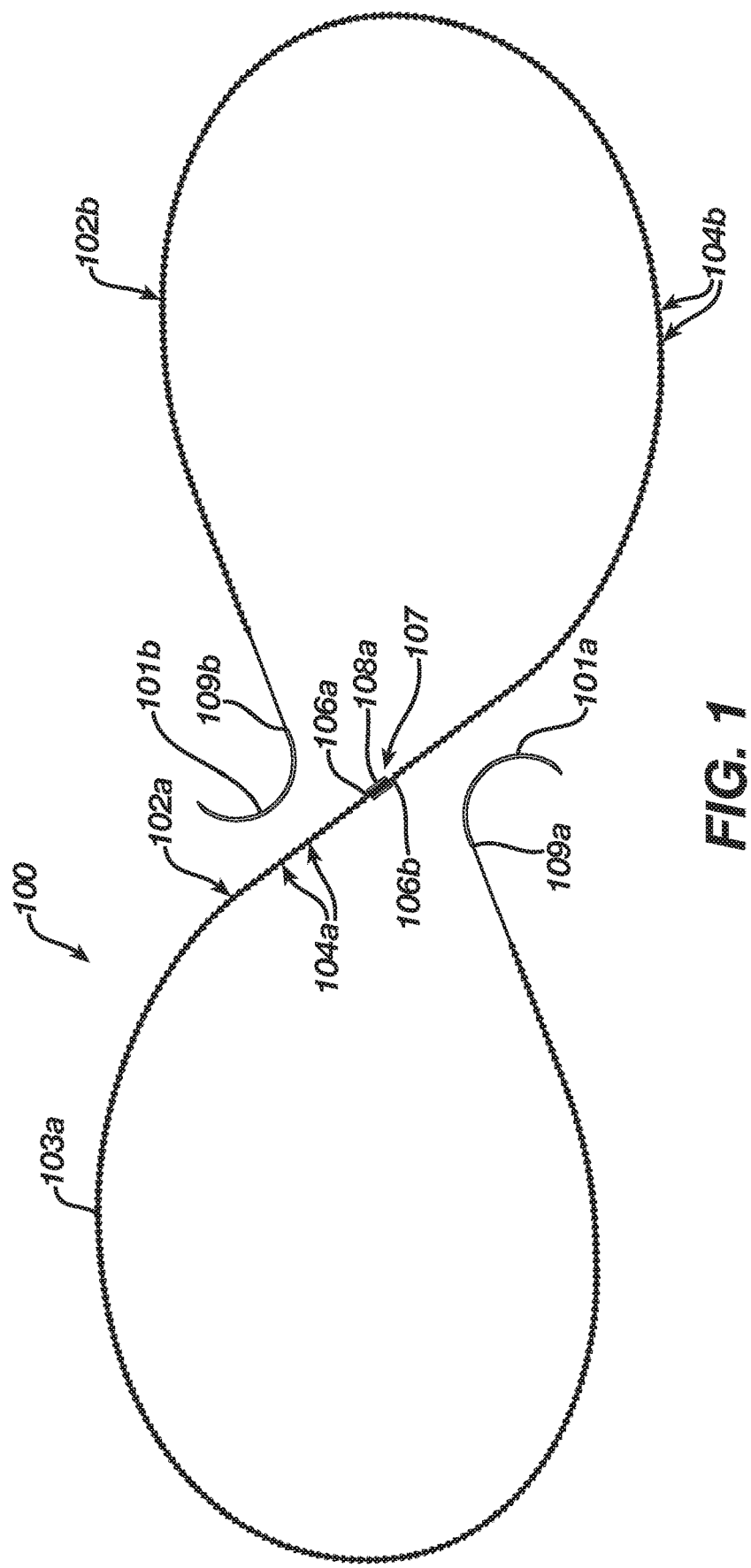
FIG. 1 illustrates a wound closure device according to at least one example herein.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, without departing from the technology. Accordingly, the drawings and descriptions should be regarded as illustrative in nature and not restrictive.

It is further understood that one or more of the teachings, expressions, embodiments, examples, etc. described herein may be combined with one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined can be readily apparent to those of ordinary skill in the art in view of the teachings herein. Such modifications and variations are intended to be included within the scope of the claims.

Figure 2:
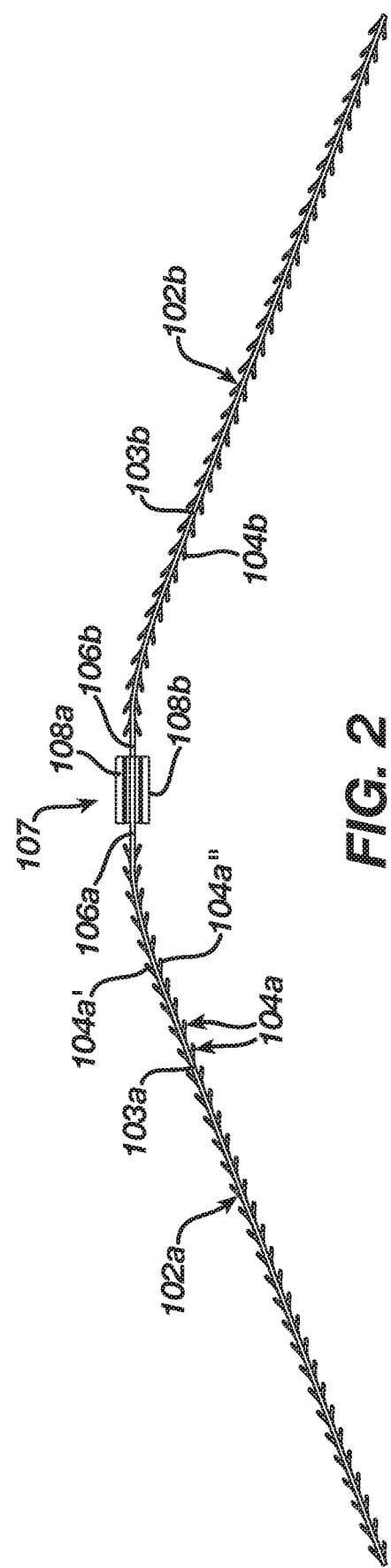
FIG. 2 depicts an enlarged view of a portion of the wound closure device of FIG.
Figure 6A:
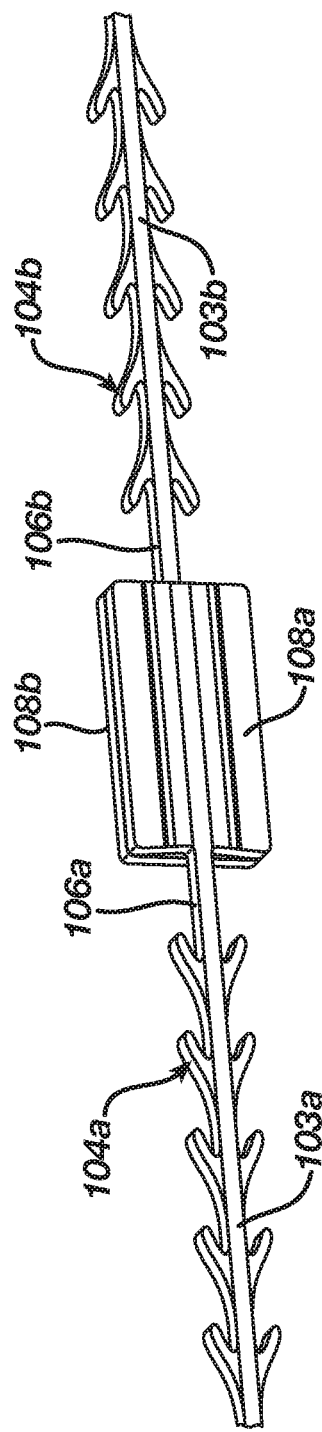
FIGS. 6A-6B depict a perspective view and side view, respectively, of the connecting section of the wound closure device of FIG. 1.
Figure 6B:
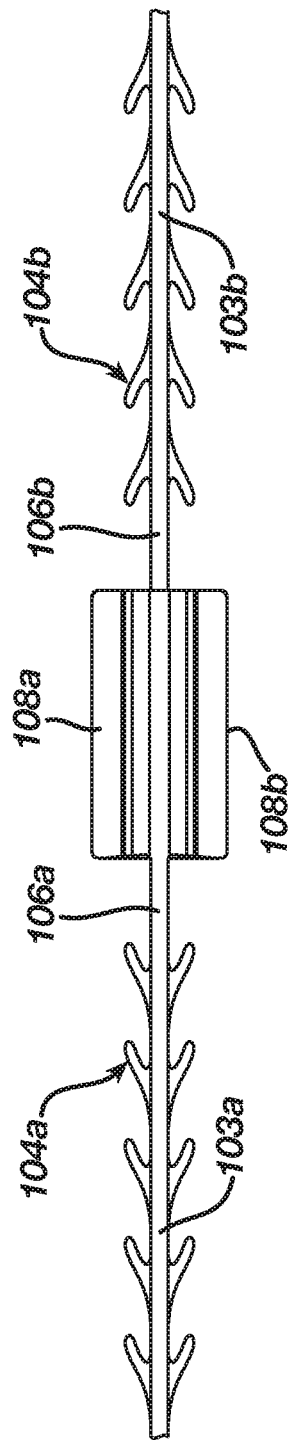

FIGS. 1-2 illustrate different views of a wound closure device 100 according to one or more examples herein. The wound closure device 100 can include a first suture segment 102a and a second suture segment 102b, and a connecting or transition section 107 therebetween. The first and second suture segments 102a, 102b can include filamentary elements 103a, 103b according to examples herein. The first and second suture segments 102a, 102b can be comprised of any suitable surgical suture material (i.e., absorbable and non-absorbable polymeric materials, metallic, or ceramic materials). As shown in FIG. 1, in one example, the first suture segment 102a can include a plurality of barbs or protrusions 104a extending outwardly from the filamentary element 103a. Further, as shown in an example, the second suture segment 102b can include a plurality of barbs or protrusions 104b extending outwardly from the filamentary element 103b. As described herein, the barbs or protrusions can function to increase the holding strength of the suture and/or eliminate the need for knot tying. Further, in the example shown in FIGS. 1-2, the barbs or protrusions 104a, 104b can be symmetric. For example, one of the barbs or protrusions 104a' can be similar in shape and to a corresponding barb 104a" and can extend from the filamentary element 103a on an opposite side (e.g., about 180 degrees) and in an opposite direction of the corresponding barb 104a". Examples of barbs such as the barbs or protrusions 104a, 104b that can be used herein can be described in more detail in U.S. Pub. No. 2014/0081321, which is incorporated herein by reference in its entirety. According to examples herein, the barbs or protrusions such as 104a, 104b can be formed by any suitable method such as being compound profile punched from preformed material in a manner described in more detail in U.S. Patent Publication No. 2007/0257395 and U.S. Pat. No. 7,850,894, which are incorporated herein by reference in their entirety.

The first and second suture segments 102a, 102b can include the same or different suture configurations. For example, the first suture segment 102a can include a filamentary element 103a and barbs or protrusions 104a with different characteristics such as barb size, filament size, material type, barb type, filament type and/or the like thereby forming a first suture configuration. Further, in an example, the second suture segment 102b can include a filamentary element 103b and barbs or protrusions 104b with different characteristics such as barb size, filament size, material type, barb type, filament type, and/or the like thereby forming a second suture configuration. In one example, the first and second suture configurations can be the same, that is, the first and second filamentary elements 103a, 103b and barbs or protrusions 104a, 104b can be the same size, material, type, and/or the like. Further, in an example, the first and second suture configurations can be different, that is, the first and second filamentary elements 103a, 103b and/or barbs or protrusions 104a, 104b can be different sizes, materials, types, and/or the like. For example, the first suture configuration can include a filamentary element 103a and barbs or protrusions 104a with a particular or selected size and/or material (e.g., a size 3-0 symmetric PDS barbed suture), but that can be undyed, and the second suture configuration can include a filamentary element 103b and barbs or protrusions 104b with the same size or materials (e.g., a size 3-0 symmetric PDS barbed suture), but that can be dyed. In such an example, the wound closure device or suture can have suture segments of different colors for appropriate visibility of a strand or segment of the suture or wound closure device in a bloody (e.g., the segment can be a dyed material for visibility therein) and a non-bloody (e.g., the segment can be an undyed material) surgical field. Examples herein can further include other combination of sizes, materials, types, and/or the like (e.g., as described herein).

In one example, the first suture segment 102a can include a first needle or insertion device 101a and the second suture segment 102b can include a second needle or insertion device 101b at a respective first and second proximal end 109a, 109b thereof. The first and second needles or insertion devices 101a, 101b can be any suitable needle or insertion devices configured to pass through tissue. Further, the first and second needles or insertion device 101a, 101b can be made of any suitable material such as steel, Ethalloy, and/or the like, can be any suitable shape and size such as straight, curved, and/or the like, and or may have any other suitable properties including tapered cut, tapered point, blunt tips, and/or the like such that the first and second needles or insertion devices 101a, 101b can be inserted and can pass through tissue to enable the first and second suture segments 102a, 102b to pass through and approximate the tissue as described herein. In an example, the first and second needles or insertion devices 101a, 101b can be the same. For example, the first and second needles or insertion devices 101a, 101b can be the same material, shape, size, and/or the like (i.e. they can have the same properties as each other). In an additional example, the first and second needles or insertion devices 101a, 101b can be different. For example, the first and second needles or insertion devices 101a, 101b can be different materials, shapes, sizes, and/or the like (i.e. they can have one or more properties that are different from each other).

As shown, the first suture segment 102a can include a first distal end 106a and the second suture segment can include a second distal end 106b. The first and second distal ends 106a, 106b can have a fixation tab or stop element 108a and 108b, respectively, attached thereto or formed therefrom. The first and second fixation tabs 108a, 108b can be joined together using various methods such as lamination as described herein to form the transition zone 107 (e.g., the connecting section) between the first and second suture segments 102a, 102b. As such, in examples herein, the fixation tabs or stop elements can provide an adequate surface area to laminate two fixation tab surfaces together using RF energy or other means of joining dissimilar materials together to create the bi-directional strand. Further, in examples herein, the transition zone or connecting section 107 can be a transition point between one suture segment and another suture segment (e.g., a transition point between two sutures connected together as described herein). Additionally, according to one or more examples, the transition zone or connecting section 107 and each respective fixation tab or stop element can provides a tactile indicator to the user of the wound closure device that each leg may be appropriately seated in tissue. After lamination, in an example, a portion of the connecting section or transition zone 107 can also be trimmed or punched away to reduce the size or change the shape of the transition zone or connecting section.

FIG. 3 depicts an exploded view of stop elements 108a, 108b of the wound closure device 100 of FIGS. 1-2, for example, prior to forming a connecting section (e.g., the transition zone 107). As shown, in an example, the stop elements 108a, 108b can include a leading edge defined by a leading edge thickness t and a leading edge width w, and also has a length l along an elongated axis of the suture. In examples, the stop elements 108a, 108b can be the same shapes, sizes, and/or the like (e.g., the same t, w, and l). Further, the stop elements 108a, 108b can be different shapes, sizes, and/or the like (e.g., as shown in FIGS. 9-14 with stop elements 308a, 308b). In some examples, one of the first and second suture segments 102a, 102b can include a stop element while the other may not include a stop element. In examples, the stop elements described herein can have a thickness (e.g., t) of about 0.010" to 0.025", a width (e.g., w) of about 0.095" to 0.120", and a length (e.g., l) of about 0.095" to about 0.200". According to one example, the length can be shorter (e.g., about 0.095") for stop element 308a than for the other stop elements (e.g., about 0.200") such as stop elements 108a, 108b, 208b, 308c, 408a, 508a, 608a, 708a, 708b, 808a, and/or the like.

FIGS. 4-6B illustrates a top view, cross-section view, perspective and side views respectively of the wound closure device of FIGS. 1-2, for example, after formation of the connecting section or transition zone 107 (e.g., after lamination of the stop elements 108a, 108b together). As shown, a first side 120a of the first stop element 108a can be joined with a first side 122a of the second stop element 108b to form the transition zone or connecting section 107. In an example, the first side 120a can be laminated directly to the first side 122a to form the transition zone or connecting section 107. Thus, in examples, at least a portion of the stop element 308a can be laminated (e.g., directly) to at least a portion of the stop element 308b. In such an example, no additional material may be used during lamination to form the transition zone or connecting section 107 and as shown, each of the suture segments or legs 102a, 102b can have its own integral end effector (e.g., the first and second stop elements 108a, 108b), for example, prior to lamination. According to one or more examples herein, to laminate the first sides 120a, 122a together, RF energy can be applied to each of the sides 120a, 122a of the tabs or stop elements 108a, 108b and the two sides to which the RF energy has been applied can then be joined together to form the transition zone or connecting section 107. According to additional examples, the sides (e.g., 120a, 122a can be laminated together by applying thermal energy (e.g., using infrared and laser technologies and/or energy), mechanical energy (e.g., using vibrational and ultrasonic technologies and/or energy), and/or the like.

To laminate the stop elements (e.g., 108a, 108b) together as described herein, the sides of the stop elements (e.g., the insulating material such as PDS from which they may be made of) can be dielectrially heated using RF lamination and/or welding. RF lamination and/or welding as described herein to form the connecting section or transition zone (e.g., 107) can include dielectric heating non-conducting or electrically insulating materials such as PDS (e.g., from which the stop elements can be made). According to examples, one or more polymer molecules of these dielectric materials includes one part of the molecule that can have a slight positive charge, while the opposite part of the molecule can have a slight negative charge. When placed in an electric field, these polar molecules can orient themselves so their positive ends face the negative part of the applied electric field and the negative ends face the positive part of the applied electric field. When applying power, the power can change the electrical field across the plates at a frequency of 13 to 100 MHz per second. For dielectric materials such as PDS, such a change in an electrical field can cause electrons to be pulled alternatively within the dielectric field and molecular friction generates heat to laminate the materials (e.g., the first sides of the stop elements such as 120a, 122a of 108a, 108b) together. Thus, according to examples herein, to laminate the stop elements together to form the connecting section or transition zone, power or energy can be applied to the stop elements (e.g., a first parameter), for a particular amount of time or duration (e.g., a second parameter), and under a particular pressure (e.g., a third parameter).

According to examples herein, laminating suture segments (e.g., 102a, 102b), which can also referred be to as legs or strands, together can enable overall device lengths that may be greater than tooling limitations may typically enable as tooling may otherwise set length maximums for individual strands. For example, equipment and tooling may limit the segment or strand length that can be achieved for a barbed suture. By using the lamination process or methods described herein, an overall length of the suture device or wound closure device can be increased. For example, by joining the segments or strands together as shown, the overall length of the suture device or wound closure device can be up to twice the length of an individual segment or strand without investing in equipment or tooling to produce an integrally-formed suture or wound closure device having the same or similar length or features.

Figure 7:
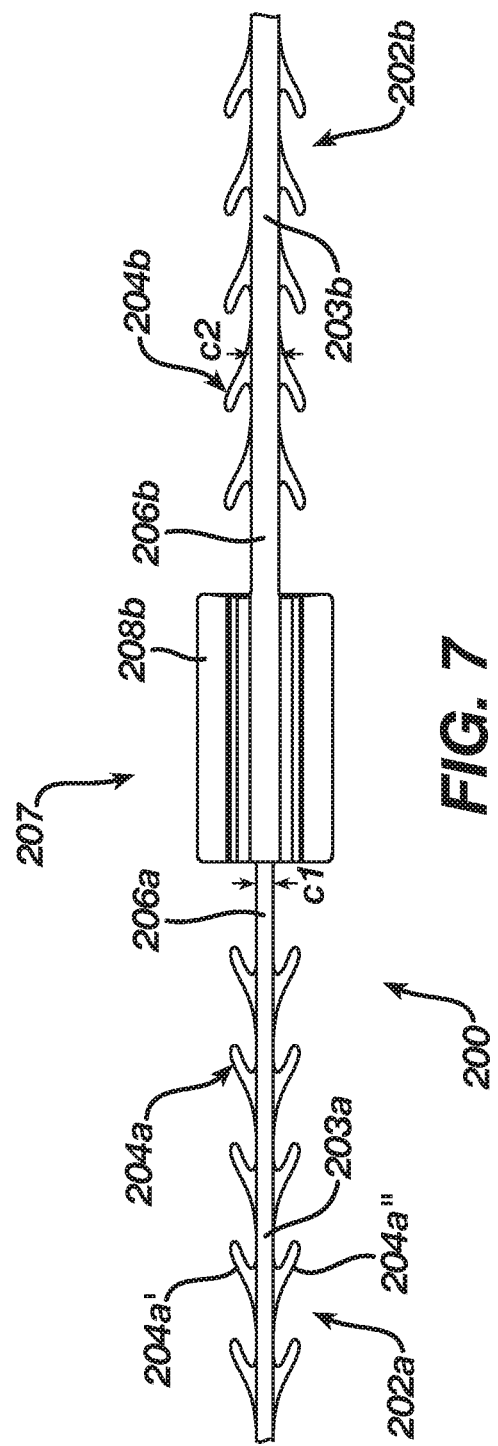
FIG. 7 illustrates another example of a wound closure device and a connecting section thereof according to an example herein.

FIG. 7 illustrates another example of a wound closure device 200 and a connecting section 207 thereof according to an example herein. As shown in FIG. 7 (e.g., similar to the example in FIGS. 1-2), the wound closure device 200 can include a first suture segment 202a and a second suture segment 202b, and a connecting or transition section 207 therebetween. The first and second suture segments 202a, 202b can include first and second filamentary elements 203a, 203b according to examples herein. As shown, the first and second filamentary elements 203a, 203b can be different sizes (e.g., a size 3-0 suture can be connected or laminated to a size 1 suture). For example, the first filamentary element 203a can have a diameter or width c1 and the second filamentary element 203b can have a diameter or width c2. In an example, the diameter c2 can be larger than the diameter c1 as shown.

As described herein, the first and second suture segments 202a, 202b can be comprised of any suitable surgical suture material (i.e., absorbable and non-absorbable polymeric materials, metallic, or ceramic materials). As shown in FIG. 7, in one example, the first suture segment 202a can include a plurality of barbs or protrusions 204a extending outwardly from the filamentary element 203a. Further, as shown in an example, the second suture segment 102b can include a plurality of barbs or protrusions 204b extending outwardly from the filamentary element 203b. As described herein, the barbs or protrusions can function to increase the holding strength of the suture and/or eliminate the need for knot tying. Further, in the example shown in FIG. 7, the barbs or protrusions 204a, 204b can be symmetric. For example, one of the barbs or protrusions 204a' can be similar in shape and to a corresponding barb 204a" and can extend from the filamentary element 203a on an opposite side (e.g., about 180 degrees) and in an opposite direction of the corresponding barb 204a". According to examples herein, the barbs or protrusions can be formed by any suitable method such as being compound profile punched from preformed material and/or any other suitable method as described herein.

The first and second suture segments 202a, 202b can include the same or different suture configurations. For example, as described above, the first suture segment 202a can include a filamentary element 203a with different characteristics such as a smaller filament size (e.g., a smaller cross-section, width, or diameter) thereby forming a first suture configuration. Further, in an example, the second suture segment 202b can include a filamentary element 203b with different characteristics such as a larger filament size (e.g., a larger cross-section, width, or diameter) thereby forming a second suture configuration. Other characteristics of each suture segment can also be the same or different such as colors or dyes, barb sizes, suture types, materials, needles and their characteristics, and/or the like as described herein.

In one example, the first suture segment 202a can include a first needle or insertion device (not shown) and the second suture segment 202b can include a second needle or insertion device (not shown) at a respective first and second proximal end thereof (e.g., as shown as an example in FIG. 1 with first and second needles 101a, 101b). The first and second needles or insertion devices can be any suitable needle or insertion devices configured to pass through tissue. Further, the first and second needles or insertion devices can be made of any suitable material such as steel, Ethalloy, and/or the like, can be any suitable shape and size such as straight, curved, and/or the like, and or may have any other suitable properties including tapered cut, tapered point, blunt tips, and/or the like such that the first and second needles or insertion devices can be inserted and can pass through tissue to enable the first and second suture segments 202a, 202b to pass through and approximate the tissue as described herein. In an example, the first and second needles or insertion devices can be the same. For example, the first and second needles or insertion devices can be the same material, shape, size, and/or the like (i.e. they can have the same properties as each other). In an additional example, the first and second needles or insertion devices can be different. For example, the first and second needles or insertion devices can be different materials, shapes, sizes, and/or the like (i.e. they can have one or more properties that are different from each other).

As shown, the first suture segment 202a can include a first distal end 206a and the second suture segment 202b can include a second distal end 206b. The first and second distal ends 206a, 206b can have a fixation tab or stop element 208a and 208b, respectively, attached thereto or formed therefrom. The first and second fixation tabs 208a, 208b can be joined together using various methods such as lamination as described herein to form the transition zone 207 (e.g., the connecting section) between the first and second suture segments 202a, 202b. As such, in examples herein, the fixation tabs or stop elements can provide an adequate surface area to laminate two fixation tab surfaces together using RF energy or other means of joining dissimilar materials together to create the bi-directional strand. Additionally, in an example (e.g., described in FIGS. 8-13B), an additional tab can be used to form the transition zone or connecting section 207. In examples herein, the transition zone or connecting section 207 can be a transition point between one suture segment and another suture segment (e.g., a transition point between two sutures connected together as described herein). Additionally, according to one or more examples, the transition zone or connecting section 207 and each respective fixation tab or stop element can provides a tactile indicator to the user of the wound closure device that each leg may be appropriately seated in tissue. After lamination, in an example, a portion of the connecting section or transition zone 207 can also be trimmed or punched away to reduce the size or change the shape of the transition zone or connecting section.

FIG. 8 illustrates another example of a wound closure device 300 and a connecting section 307 thereof according to an example herein. As shown in FIG. 8 (e.g., similar to the example in FIGS. 1-2), the wound closure device 300 can include a first suture segment 302a and a second suture segment 302b, and a connecting or transition section 307 therebetween. In an example, the wound closure device 300 can be a bi-directional barbed suture for multi-layer tissue closure that can include one suture leg or section (e.g., 302b) composed of PDS material with the appropriately sized anchor geometry and needle for fascia closure joined to another suture leg or section (e.g., 302a) composed of MONOCRYL material with the appropriately sized anchor geometry in a reverse direction and a needle appropriate for subcutaneous or subcuticular tissue closure. As described herein, the first and second suture segments 302a, 302b can be comprised of other suitable surgical suture materials (i.e., absorbable and non-absorbable polymeric materials, metallic, or ceramic materials).

The first and second suture segments 302a, 302b can further include first and second filamentary elements 303a, 303b according to examples herein. As shown in FIG. 8, in one example, the first suture segment 302a can include a plurality of barbs or protrusions 304a extending outwardly from the filamentary element 303a. Further, as shown in an example, the second suture segment 302b can include a plurality of barbs or protrusions 304b extending outwardly from the filamentary element 303b. As described herein, the barbs or protrusions can function to increase the holding strength of the suture and/or eliminate the need for knot tying and each segment or section (e.g., 302a, 302b) can include different barbs as shown in FIG. 8 or the same barbs (e.g., as described herein and shown in FIGS. 1 and 7). The barbs or protrusions 204a, 204b can be symmetric. For example, one of the barbs or protrusions 304a' can be similar in shape and to a corresponding barb 304a" and can extend from the filamentary element 303a on an opposite side (e.g., about 180 degrees) and in an opposite direction of the corresponding barb 304a". According to examples herein, the barbs or protrusions can be formed by any suitable method such as being compound profile punched from preformed material and/or any other suitable method as described herein.

The first and second suture segments 302a, 302b can include the same or different suture configurations. For example, as described above, the first suture segment 302a can include a material such as MONOCRYL material with barbs having a first geometry and/or size as shown thereby forming a first suture configuration. Further, in an example, the second suture segment 302b can include a different material than the first suture segment 302a such as PDS with barbs having a second geometry and/or as shown thereby forming a second suture configuration. Other characteristics of each suture segment can also be the same or different such as filament sizes, colors or dyes, suture types, needles and their characteristics, and/or the like as described herein.

In one example, the first suture segment 302a can include a first needle or insertion device (not shown) and the second suture segment 302b can include a second needle or insertion device (not shown) at a respective first and second proximal end thereof (e.g., as shown as an example in FIG. 1 with first and second needles 101a, 101b). The first and second needles or insertion devices can be any suitable needle or insertion devices configured to pass through tissue. Further, the first and second needles or insertion devices can be made of any suitable material such as steel, Ethalloy, and/or the like, can be any suitable shape and size such as straight, curved, and/or the like, and or may have any other suitable properties including tapered cut, tapered point, blunt tips, and/or the like such that the first and second needles or insertion devices can be inserted and can pass through tissue to enable the first and second suture segments 302a, 302b to pass through and approximate the tissue as described herein. In an example, the first and second needles or insertion devices can be the same. For example, the first and second needles or insertion devices can be the same material, shape, size, and/or the like (i.e. they can have the same properties as each other). In an additional example, the first and second needles or insertion devices can be different. For example, the first and second needles or insertion devices can be different materials, shapes, sizes, and/or the like (i.e. they can have one or more properties that are different from each other).

As shown, the first suture segment 302a can include a first distal end 306a and the second suture segment 202b can include a second distal end 306b. The first and second distal ends 306a, 306b can have a fixation tab or stop element 308a and 308b, respectively, attached thereto or formed therefrom. The first and second fixation tabs 308a, 308b can be joined together using various methods such as lamination as described herein to form the transition zone 307 (e.g., the connecting section) between the first and second suture segments 302a, 302b. As such, in examples herein, the fixation tabs or stop elements can provide an adequate surface area to laminate two fixation tab surfaces together using RF energy or other means of joining dissimilar materials together to create the bi-directional strand. Additionally, in an example such as that shown in FIGS. 8-13B, an additional tab can be used to form the transition zone or connecting section 307. In examples herein, the transition zone or connecting section 307 can be a transition point between one suture segment and another suture segment (e.g., a transition point between two sutures connected together as described herein). Additionally, according to one or more examples, the transition zone or connecting section 307 and each respective fixation tab or stop element can provides a tactile indicator to the user of the wound closure device that each leg may be appropriately seated in tissue. After lamination, in an example, a portion of the connecting section or transition zone 307 can also be trimmed or punched away to reduce the size or change the shape of the transition zone or connecting section.

FIGS. 9-11 depicts an exploded view of stop elements and/or tabs of the wound closure device 300 of FIG. 8, for example, prior to forming the connecting section (e.g., or transition zone 307). As shown, in an example, the stop element 308a can be generally be a rounded rectangular shape (e.g., a rectangle with a rounded side as shown in FIG. 10) and can include a leading edge defined by a leading edge thickness t1 and a leading edge width w1, and also has a length l1 along an elongated axis of the suture. Further, the stop element 308b can generally be rectangular shaped and can include a leading edge defined by a leading edge thickness t1' and a leading edge width w1', and also has a length l1' along an elongated or longitudinal axis of the suture. Thus, in an example as shown, the stop elements 308a, 308b can be different shapes and/or sizes.

Further, according to an example, an additional stop element 303c (e.g., a third stop element) shown in FIG. 9, not attached to or integrally formed with the first and second filaments 303a, 303b, can be used to form the connecting section 307 as described herein. As shown, the stop element 308c can generally be rectangular shaped and can include a leading edge defined by a leading edge thickness t1" and a leading edge width w1", and also has a length l1" along an elongated or longitudinal axis of the suture. The stop element 308c can be similar in same and size as the stop element 302b according to an example as shown.

FIGS. 12-13B illustrates a top view and cross-section view, respectively, of the wound closure device of FIGS. 8-11, for example, after formation of the connecting section or transition zone 307 (e.g., after lamination of the stop elements 308a, 308b, 308c together). As shown, a first side 320a of the first stop element 308a can be joined with a first side 322a of the second stop element 308b and a second side 320b of the first stop element 308a can be joined with a first side 324a of the stop element 308c to form the transition zone or connecting section 307. In an example, the first side 320a can be laminated directly to the first side 322a and the second side 320b can be laminated directly to the first side 324a to form the transition zone or connecting section 307. Further, at least a portion of first side 322a can be laminated to first side 324a as shown. Thus, in examples, at least a portion of the stop element 308a can be laminated to at least a portion of the stop elements 308b and 308c and/or a portion of the stop elements 308b and 308c can be laminated (e.g., directly) to each other. In such an example, no additional material may be used during lamination to form the transition zone or connecting section 307 and as shown, each of the suture segments or legs 102a, 102b can have its own integral end effector (e.g., the first and second stop elements 108a, 108b), for example, prior to lamination that can be stacked with the end effector 308c. According to one or more examples herein, to laminate the first sides 320a, 322a, the second side 320b and first side 324a, and/or the first sides 322a, 324a together, RF energy can be applied to each of the sides 320a, 320b, 322a, 324a of the tabs or stop elements 308a, 308b, 308c and the sides to which the RF energy has been applied can then be joined together to form the transition zone or connecting section 307 as described herein (e.g., above).

According to examples herein, laminating suture segments (e.g., 302a, 302b), which can also referred be to as legs or strands, together can enable overall device lengths that may be greater than tooling limitations may typically enable as tooling may otherwise set length maximums for individual strands. For example, equipment and tooling may limit the segment or strand length that can be achieved for a barbed suture. By using the lamination process or methods described herein, an overall length of the suture device or wound closure device can be increased. For example, by joining the segments or strands together as shown, the overall length of the suture device or wound closure device can be up to twice the length of an individual segment or strand without investing in equipment or tooling to produce an integrally-formed suture or wound closure device having the same or similar length or features.

FIG. 14 illustrates another example of a wound closure device 400 and a connecting section 407 thereof according to an example herein. As shown in FIG. 14, the wound closure device 400 can include a first suture segment 402a and a second suture segment 402b, and a connecting or transition section 407 therebetween. The first and second suture segments 402a, 402b can include first and second filamentary elements 403a, 403b according to examples herein. As shown, the first and second filamentary elements 403a, 403b can be different sizes (e.g., a size 0 suture can be connected or laminated to a size 3-0 suture).

As described herein, the first and second suture segments 402a, 402b can be comprised of any suitable surgical suture material (i.e., absorbable and non-absorbable polymeric materials, metallic, or ceramic materials). In an example, the first and second suture segments 402a, 402b can be comprised of the same material such as PDS. In other examples, the first and second suture segments can be comprised of different materials As shown in FIG. 14, in one example, the first suture segment 402a can include a plurality of barbs or protrusions 404a extending outwardly from the filamentary element 403a. Further, as shown in an example, the second suture segment 402b can include a plurality of barbs or protrusions 404b extending outwardly from the filamentary element 403b. As described herein, the barbs or protrusions can function to increase the holding strength of the suture and/or eliminate the need for knot tying.

In an example, as shown in FIG. 14, the barbs or protrusions 404a can be symmetric. For example, barbs or protrusions 404a' can be similar in shape and to a corresponding barb 404a" and can extend from the filamentary element 403a on an opposite side (e.g., about 180 degrees) and in an opposite direction of the corresponding barb 404a". According to examples herein, the barbs or protrusions 404a can be formed by any suitable method such as being compound profile punched from preformed material and/or any other suitable method as described herein.

Further, in an example, and the barbs or protrusions 404b can be asymmetric or spiral. For example, the barbs or protrusions 404b can be formed around or in the filament 403b in an asymmetric pattern such as a spiral pattern such that a barb 404b' can be cut in the filament 403b or formed thereon asymmetrically (or spirally) from an adjacent barb 404b". In an example, the asymmetric pattern can be a spiral pattern such that the barbs including barbs 404b' and 404b" are cut in or formed in a spiral on the filament 403b. The barbs or protrusions such as the barbs or protrusions 404b can be cut or formed in any other asymmetric pattern. Examples of barbs such as the barbs or protrusions 404b that can be used herein can be described in more detail in U.S. Pat. Nos. 8,721,681 and 8,721,664, which are incorporated herein by reference in their entirety. According to examples herein, the barbs or protrusions such as 404b can be formed by any suitable method such as being cut, etched, injected molded, laser cut or formed, and/or the like such as using example methods described in more detail in U.S. Pat. No. 6,848,152, which is incorporated herein by reference in its entirety.

The first and second suture segments 402a, 402b can include different suture configurations. For example, as described above, the first suture segment 402a can include barbs 404a with different characteristics such as symmetric barbs thereby forming a first suture configuration. Further, in an example, the second suture segment 402b can include barbs 404b with different characteristics such as asymmetric or spiral barbs thereby forming a second suture configuration. Other characteristics of each suture segment can also be the same or different such as colors or dyes, filament sizes or characteristics, barb sizes, suture types, materials, needles and their characteristics, and/or the like as described herein.

In one example, the first suture segment 402a can include a first needle or insertion device (not shown) and the second suture segment 402b can include a second needle or insertion device (not shown) at a respective first and second proximal end thereof (e.g., as shown as an example in FIG. 1 with first and second needles 101a, 101b). The first and second needles or insertion devices can be any suitable needle or insertion devices configured to pass through tissue. Further, the first and second needles or insertion devices can be made of any suitable material such as steel, Ethalloy, and/or the like, can be any suitable shape and size such as straight, curved, and/or the like, and or may have any other suitable properties including tapered cut, tapered point, blunt tips, and/or the like such that the first and second needles or insertion devices can be inserted and can pass through tissue to enable the first and second suture segments 402a, 402b to pass through and approximate the tissue as described herein. In an example, the first and second needles or insertion devices can be the same. For example, the first and second needles or insertion devices can be the same material, shape, size, and/or the like (i.e. they can have the same properties as each other). In an additional example, the first and second needles or insertion devices can be different. For example, the first and second needles or insertion devices can be different materials, shapes, sizes, and/or the like (i.e. they can have one or more properties that are different from each other).

As shown, the first suture segment 402a can include a first distal end 406a and the second suture segment 402b can include a second distal end 406b. The first distal end 406a can have a fixation tab or stop element 408a attached thereto or formed therefrom. The first fixation tab 408a can be joined together with the distal end 406b of the second suture segment and an additional tab (not shown) using various methods such as lamination as described herein to form the transition zone 407 (e.g., the connecting section). For example, in an example, an additional tab can be used to form the transition zone or connecting section 407 by laminating the first stop element 408a to the distal end 406b of the second suture segment and an additional tab forming a stacked pattern (e.g., similar to that described in FIGS. 8-13B). As such, in examples herein, the fixation tab or stop elements can provide an adequate surface area to laminate the first and second suture segments 402a, 402b together using RF energy or other means of joining dissimilar materials together to create the bi-directional strand. In examples herein, the transition zone or connecting section 407 can be a transition point between one suture segment and another suture segment (e.g., a transition point between two sutures connected together as described herein). Additionally, according to one or more examples, the transition zone or connecting section 407 and each respective fixation tab or stop element can provides a tactile indicator to the user of the wound closure device that each leg may be appropriately seated in tissue. After lamination, in an example, a portion of the connecting section or transition zone 407 can also be trimmed or punched away to reduce the size or change the shape of the transition zone or connecting section.

FIG. 15 illustrates another example of a wound closure 500 device and a connecting section 507 thereof according to an example herein. As shown in FIG. 15, the wound closure device 500 can include a first suture segment 502a and a second suture segment 502b, and a connecting or transition section 507 therebetween. The first and second suture segments 502a, 502b can include first and second filamentary elements 503a, 503b according to examples herein. As shown, the first and second filamentary elements 503a, 503b can be different sizes (e.g., a size 0 suture can be connected or laminated to a size 3-0 suture) and can be different colors (e.g., dyed and undyed).

As described herein, the first and second suture segments 502a, 502b can be comprised of any suitable surgical suture material (i.e., absorbable and non-absorbable polymeric materials, metallic, or ceramic materials). In an example, the first and second suture segments can be comprised of different materials such as PDS and MONOCRYL (e.g., the first suture segment 502a can be comprised of PDS and the second suture segment 502b can be comprised of MONOCRYL). In other examples, the first and second suture segments 502a, 502b can be comprised of the same material.

As shown in FIG. 15, in one example, the first suture segment 502a can include a plurality of barbs or protrusions 504a extending outwardly from the filamentary element 503a. As described herein, the barbs or protrusions can function to increase the holding strength of the suture and/or eliminate the need for knot tying. Further, as shown in an example, the second suture segment 502b can include a non-barbed suture such as a monofilament suture.

In an example, as shown in FIG. 15, the barbs or protrusions 504a can be symmetric. For example, barbs or protrusions 504a' can be similar in shape and to a corresponding barb 504a" and can extend from the filamentary element 203a on an opposite side (e.g., about 180 degrees) and in an opposite direction of the corresponding barb 504a". According to examples herein, the barbs or protrusions 504a can be formed by any suitable method such as being compound profile punched from preformed material and/or any other suitable method as described herein.

The first and second suture segments 502a, 502b can include different suture configurations. For example, as described above, the first suture segment 502a can include barbs 404a with different characteristics such as symmetric barbs thereby forming a first suture configuration, can be dyed, and can have a filament of a first size. Further, in an example, the second suture segment 502b can be a monofilament suture, can be un-dyed, and can a filament of a second size that can be different than the first size. Other characteristics of each suture segment can also be the same or different as described herein.

In one example, the first suture segment 502a can include a first needle or insertion device (not shown) and the second suture segment 502b can include a second needle or insertion device (not shown) at a respective first and second proximal end thereof (e.g., as shown as an example in FIG. 1 with first and second needles 101a, 101b). The first and second needles or insertion devices can be any suitable needle or insertion devices configured to pass through tissue. Further, the first and second needles or insertion devices can be made of any suitable material such as steel, Ethalloy, and/or the like, can be any suitable shape and size such as straight, curved, and/or the like, and or may have any other suitable properties including tapered cut, tapered point, blunt tips, and/or the like such that the first and second needles or insertion devices can be inserted and can pass through tissue to enable the first and second suture segments 502a, 502b to pass through and approximate the tissue as described herein. In an example, the first and second needles or insertion devices can be the same. For example, the first and second needles or insertion devices can be the same material, shape, size, and/or the like (i.e. they can have the same properties as each other). In an additional example, the first and second needles or insertion devices can be different. For example, the first and second needles or insertion devices can be different materials, shapes, sizes, and/or the like (i.e. they can have one or more properties that are different from each other).

As shown, the first suture segment 502a can include a first distal end 506a and the second suture segment 502b can include a second distal end 506b. The first distal end 506a can have a fixation tab or stop element 508a attached thereto or formed therefrom. The first fixation tab or stop element 508*a* can be joined together with the distal end 506*b* of the second suture segment and an additional tab or stop element (not shown) using various methods such as lamination as described herein to form the transition zone 507 (e.g., the connecting section). For example, in an example, an additional tab can be used to form the transition zone or connecting section 507 by laminating the first stop element 508*a* to the distal end 506*b* of the second suture segment 502*b* and an additional tab forming a stacked pattern (e.g., similar to that described in FIGS. 8-13B). As such, in examples herein, the fixation tab or stop elements can provide an adequate surface area to laminate the first and second suture segments 502*a*, 502*b* together using RF energy or other means of joining dissimilar materials together to create the bi-directional strand. In examples herein, the transition zone or connecting section 507 can be a transition point between one suture segment and another suture segment (e.g., a transition point between two sutures connected together as described herein). Additionally, according to one or more examples, the transition zone or connecting section 507 and each respective fixation tab or stop element can provides a tactile indicator to the user of the wound closure device that each leg may be appropriately seated in tissue. After lamination, in an example, a portion of the connecting section or transition zone 507 can also be trimmed or punched away to reduce the size or change the shape of the transition zone or connecting section.

Figure 16:
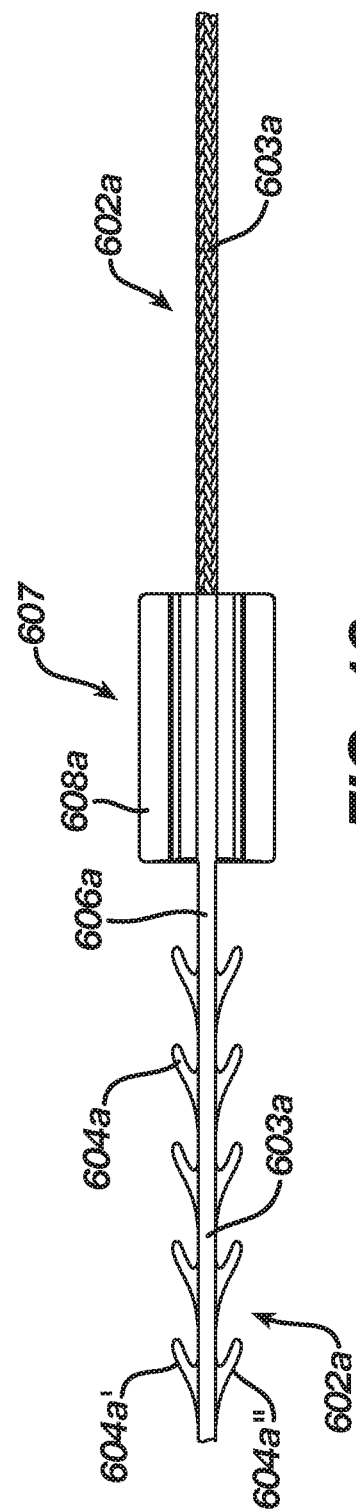
FIG. 16 illustrates another example of a wound closure device and a connecting section thereof according to an example herein.

FIG. 16 illustrates another example of a wound closure device 600 and a connecting section 607 thereof according to an example herein. As shown in FIG. 16, the wound closure device 600 can include a first suture segment 602*a* and a second suture segment 602*b*, and a connecting or transition section 607 therebetween. The first and second suture segments 602*a*, 602*b* can include first and second filamentary elements 603*a*, 603*b* according to examples herein. As shown, the first and second filamentary elements 603*a*, 603*b* can be different sizes (e.g., a size 0 suture can be connected or laminated to a size 2-0 suture).

As described herein, the first and second suture segments 602*a*, 602*b* can be comprised of any suitable surgical suture material (i.e., absorbable and non-absorbable polymeric materials, metallic, or ceramic materials). In an example, the first and second suture segments can be comprised of different materials such as PDS and VICRYL (e.g., the first suture segment 602*a* can be comprised of PDS and the second suture segment 602*b* can be comprised of VICRYL). In other examples, the first and second suture segments 602*a*, 602*b* can be comprised of the same material.

As shown in FIG. 16, in one example, the first suture segment 602*a* can include a plurality of barbs or protrusions 604*a* extending outwardly from the filamentary element 603*a*. As described herein, the barbs or protrusions can function to increase the holding strength of the suture and/or eliminate the need for knot tying. Further, as shown in an example, the second suture segment 602*b* can include a non-barbed suture such as a multi-filament suture.

In an example, as shown in FIG. 16, the barbs or protrusions 504*a* can be symmetric. For example, barbs or protrusions 604*a*' can be similar in shape and to a corresponding barb 604*a*" and can extend from the filamentary element 603*a* on an opposite side (e.g., about 180 degrees) and in an opposite direction of the corresponding barb 604*a*". According to examples herein, the barbs or protrusions 604*a* can be formed by any suitable method such as being compound profile punched from preformed material and/or any other suitable method as described herein.

The first and second suture segments 602*a*, 602*b* can include different suture configurations. For example, as described above, the first suture segment 602*a* can include barbs 604*a* with different characteristics such as symmetric barbs thereby forming a first suture configuration and can have a filament of a first size. Further, in an example, the second suture segment 602*b* can be a multi-filament suture and can have a filament of a second size that can be different than the first size. Other characteristics of each suture segment can also be the same or different as described herein.

In one example, the first suture segment 602*a* can include a first needle or insertion device (not shown) and the second suture segment 602*b* can include a second needle or insertion device (not shown) at a respective first and second proximal end thereof (e.g., as shown as an example in FIG. 1 with first and second needles 101*a*, 101*b*). The first and second needles or insertion devices can be any suitable needle or insertion devices configured to pass through tissue. Further, the first and second needles or insertion devices can be made of any suitable material such as steel, Ethalloy, and/or the like, can be any suitable shape and size such as straight, curved, and/or the like, and or may have any other suitable properties including tapered cut, tapered point, blunt tips, and/or the like such that the first and second needles or insertion devices can be inserted and can pass through tissue to enable the first and second suture segments 602*a*, 602*b* to pass through and approximate the tissue as described herein. In an example, the first and second needles or insertion devices can be the same. For example, the first and second needles or insertion devices can be the same material, shape, size, and/or the like (i.e. they can have the same properties as each other). In an additional example, the first and second needles or insertion devices can be different. For example, the first and second needles or insertion devices can be different materials, shapes, sizes, and/or the like (i.e. they can have one or more properties that are different from each other).

As shown, the first suture segment 602*a* can include a first distal end 606*a* and the second suture segment 602*b* can include a second distal end 606*b*. The first distal end 606*a* can have a fixation tab or stop element 608*a* attached thereto or formed therefrom. The first fixation tab or stop element 608*a* can be joined together with the distal end 606*b* of the second suture segment and an additional tab or stop element (not shown) using various methods such as lamination as described herein to form the transition zone 607 (e.g., the connecting section). For example, in an example, an additional tab can be used to form the transition zone or connecting section 607 by laminating the first stop element 608*a* to the distal end 606*b* of the second suture segment 602*b* and an additional tab forming a stacked pattern (e.g., similar to that described in FIGS. 8-13B). As such, in examples herein, the fixation tab or stop elements can provide an adequate surface area to laminate the first and second suture segments 602*a*, 602*b* together using RF energy or other means of joining dissimilar materials together to create the bi-directional strand. In examples herein, the transition zone or connecting section 607 can be a transition point between one suture segment and another suture segment (e.g., a transition point between two sutures connected together as described herein). Additionally, according to one or more examples, the transition zone or connecting section 607 and each respective fixation tab or stop element can provides a tactile indicator to the user of the wound closure device that each leg may be appropriately seated in tissue. After lamination, in an example, a portion of the connecting section or transition zone 607 can also be trimmed or punched away to reduce the size or change the shape of the transition zone or connecting section.

Figure 17:
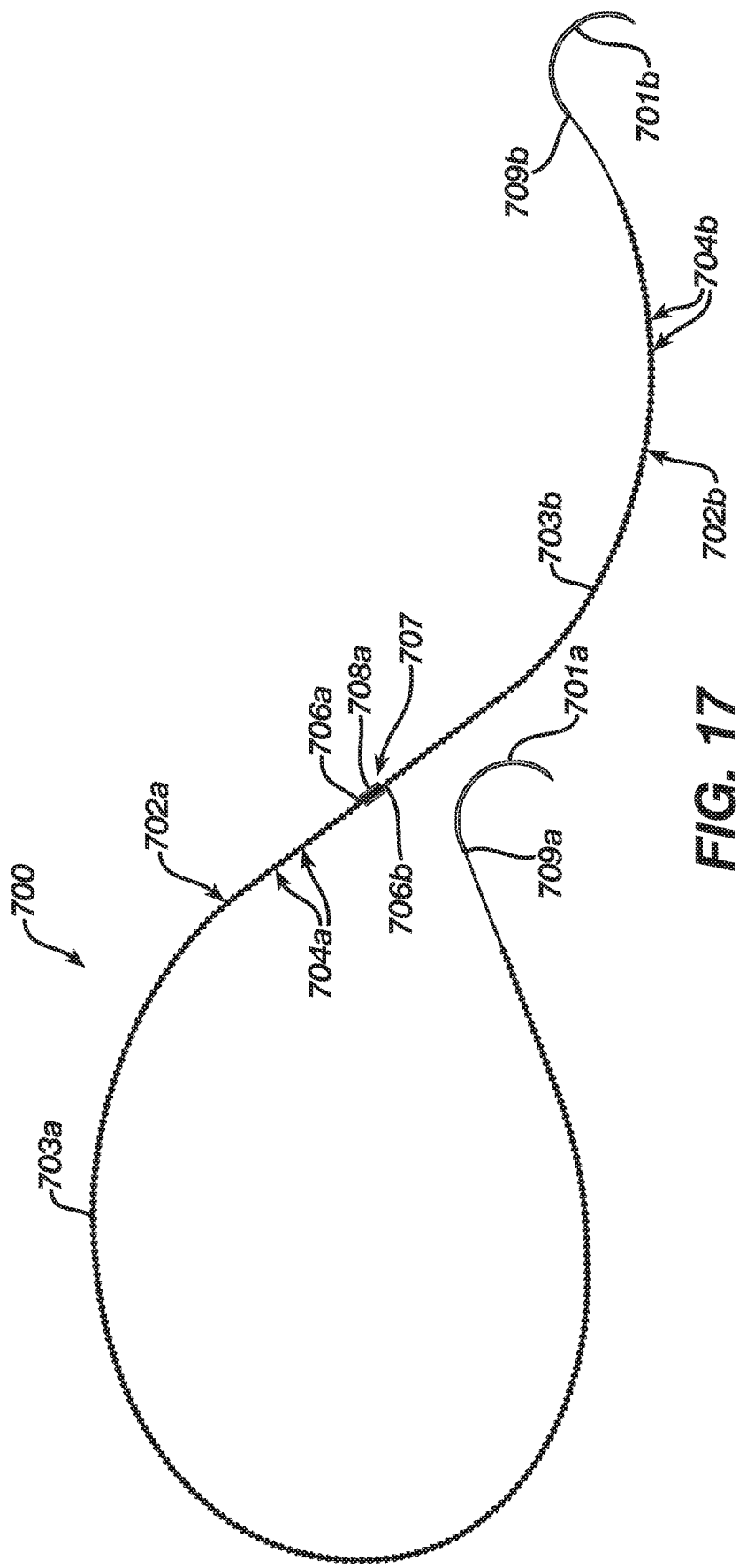
FIG. 17 illustrates another example of a wound closure device and a connecting section thereof according to an example herein.

FIG. 17 illustrates another example of a wound closure device 700 and a connecting section 707 thereof according to an example herein. In examples, the wound closure device 700 can have one or more of the other example features or properties of the wound closure devices described herein. For example, as shown in FIG. 17, the wound closure device 700 can include a first suture segment 702*a* and a second suture segment 702*b*, and a connecting or transition section 707 therebetween. The first and second suture segments 702*a*, 702*b* can include first and second filamentary elements 703*a*, 703*b* according to examples herein. As shown, the first and second filamentary elements 703*a*, 703*b* can be different lengths (e.g., the first filamentary element 703*a* can be longer than the second filamentary element 703*b*).

As described herein, the first and second suture segments 702*a*, 702*b* can be comprised of any suitable surgical suture material (i.e., absorbable and non-absorbable polymeric materials, metallic, or ceramic materials). In an example, the first and second suture segments can be comprised of different materials such as PDS and VICRYL (e.g., the first suture segment 702*a* can be comprised of PDS and the second suture segment 702*b* can be comprised of VICRYL). In other examples, the first and second suture segments 702*a*, 702*b* can be comprised of the same material.

As shown in FIG. 17, in one example, the first suture segment 702*a* can include a plurality of barbs or protrusions 704*a* extending outwardly from the filamentary element 403*a*. Further, as shown in an example, the second suture segment 702*b* can include a plurality of barbs or protrusions 404*b* extending outwardly from the filamentary element 703*b*. As described herein, the barbs or protrusions can function to increase the holding strength of the suture and/or eliminate the need for knot tying.

In an example, as shown in FIG. 17, the barbs or protrusions 704*a*, 704*b* can be symmetric. For example, barbs or protrusions 704*a*, 704*b* can be similar in shape and to a corresponding barb and can extend from the filamentary element 703*a*, 703*b* on an opposite side (e.g., about 180 degrees) and in an opposite direction of the corresponding barb. According to examples herein, the barbs or protrusions 704*a*, 704*b* can be formed by any suitable method such as being compound profile punched from preformed material and/or any other suitable method as described herein.

Further, in an example, and the barbs or protrusions 704*a*, 704*b* can be asymmetric or spiral (not shown). For example, the barbs or protrusions 704*a*, 704*b* can be formed around or in the filament in an asymmetric pattern such as a spiral pattern such that a barb can be cut in the filament or formed thereon asymmetrically (or spirally) from an adjacent barb. In an example, the asymmetric pattern can be a spiral pattern such that the barbs including barbs and are cut in or formed in a spiral on the filament. The barbs or protrusions such as the barbs or protrusions can be cut or formed in any other asymmetric pattern. Examples of barbs such as the barbs or protrusions 404*b* that can be used herein can be described in more detail in U.S. Pat. Nos. 8,721,681 and 8,721,664, which are incorporated herein by reference in their entirety. According to examples herein, the barbs or protrusions such as can be formed by any suitable method such as being cut, etched, injected molded, laser cut or formed, and/or the like such as using example methods described in more detail in U.S. Pat. No. 6,848,152, which is incorporated herein by reference in its entirety.

In yet another example, one or more of the first or second suture segments 702*a*, 702*b* can include a monofilament or multi-filament suture as described herein with different lengths, characteristics, and/or the like. As such, the suture segments 702*a*, 702*b* can include barbed, non-barbed, and/or any other suture types and characteristics.

For example, the first and second suture segments 702*a*, 702*b* can include different suture configurations. For example, as described above, the first suture segment 702*a* can include a first length thereby forming a first suture configuration. Further, in an example, the second suture segment 702*b* can be a second length thereby forming a second suture configuration. Other characteristics of each suture segment can also be the same or different such as colors or dyes, filament sizes or characteristics, barb sizes, suture types, materials, needles and their characteristics, and/or the like as described herein.

In one example, the first suture segment 702*a* can include a first needle or insertion device 701*a* and the second suture segment 702*b* can include a second needle or insertion device 701*b* at a respective first and second proximal end thereof. The first and second needles or insertion devices 701*a*, 701*b* can be any suitable needle or insertion devices configured to pass through tissue. Further, the first and second needles 701*a*, 701*b* or insertion devices can be made of any suitable material such as steel, Ethalloy, and/or the like, can be any suitable shape and size such as straight, curved, and/or the like, and or may have any other suitable properties including tapered cut, tapered point, blunt tips, and/or the like such that the first and second needles or insertion devices 701*a*, 701*b* can be inserted and can pass through tissue to enable the first and second suture segments 702*a*, 702*b* to pass through and approximate the tissue as described herein. In an example, the first and second needles or insertion devices can be the same. For example, the first and second needles or insertion devices 701*a*, 701*b* can be the same material, shape, size, and/or the like (i.e. they can have the same properties as each other). In an additional example, the first and second needles or insertion devices can be different. For example, the first and second needles or insertion devices 701*a*, 701*b* can be different materials, shapes, sizes, and/or the like (i.e. they can have one or more properties that are different from each other).

As shown, the first suture segment 702*a* can include a first distal end 706*a* and the second suture segment 702*b* can include a second distal end 706*b*. The first and second distal ends 706*a*, 706*b* can have a first fixation tab or stop element 708*a* and a second fixation tab or stop element (not shown), respectively, attached thereto or formed therefrom. The first and second fixation tabs can be joined together using various methods such as lamination as described herein to form the transition zone 707 (e.g., the connecting section) between the first and second suture segments 702*a*, 702*b*. As such, in examples herein, the fixation tabs or stop elements can provide an adequate surface area to laminate two fixation tab surfaces together using RF energy or other means of joining dissimilar materials together to create the bi-directional strand. Additionally, in an example (e.g., described in FIGS. 8-13B), an additional tab can be used to form the transition zone or connecting section 707. In examples herein, the transition zone or connecting section 707 can be a transition point between one suture segment and another suture segment (e.g., a transition point between two sutures connected together as described herein). Additionally, according to one or more examples, the transition zone or connecting section 707 and each respective fixation tab or stop element can provides a tactile indicator to the user of the wound closure device that each leg may be appropriately seated in tissue. After lamination, in an example, a portion of the connecting section or transition zone 707 can also be trimmed or punched away to reduce the size or change the shape of the transition zone or connecting section.

FIG. 18 illustrates another example of a wound closure device 800 and a connecting section 807 thereof according to an example herein. In examples, the wound closure device 800 can have one or more of the other example features or properties of the wound closure devices described herein. For example, as shown in FIG. 18, the wound closure device 800 can include a first suture segment 802a, a second suture segment 802b, and a third suture segment 802c and a connecting or transition section 807 therebetween. In examples, as shown in dotted lines, the wound closure device 800 can further include additional suture segments such that the wound closure device 800 can have suitable characteristic and/or the like to close a wound.

The first, second, and third suture segments 802a, 802b, 802c can include respective filamentary elements according to examples herein. As described herein, the first, second, and third suture segments 802a, 802b, 802c can be comprised of any suitable surgical suture material (i.e., absorbable and non-absorbable polymeric materials, metallic, or ceramic materials). In an example, the first, second, and third suture segments 802a, 802b, 802c can be comprised of different materials such as PDS and VICRYL (e.g., the first suture segment 802a can be comprised of PDS and the second and third suture segments 802b can be comprised of VICRYL and/or any other combination thereof). In other examples, the first, second, and third suture segments 802a, 802b, 802c can be comprised of the same material.

As shown in FIG. 18, in one example, the first, second, and third suture segments 802a, 802b, 802c can include a plurality of barbs or protrusions extending outwardly from the filamentary element. As described herein, the barbs or protrusions can function to increase the holding strength of the suture and/or eliminate the need for knot tying. The barbs or protrusions can be symmetric as described herein. Additionally, in examples, the barbs or protrusions can be asymmetric or spiral (not shown) as described herein. In yet another example, one or more of the first, second, and third suture segments 802a, 802b, 802c can include a monofilament or multi-filament suture as described herein with different lengths, characteristics, and/or the like. As such, the first, second, and third suture segments 802a, 802b, 802c can include barbed, non-barbed, and/or any other suture types and characteristics.

For example, the first, second, and third suture segments 802a, 802b, 802c can include different suture configurations. For example, as described above, the first suture segment 802a can include a first set of characteristics or features thereby forming a first suture configuration. Further, in an example, the second suture segment 802b can include a second set of characteristics or features thereby forming a second suture configuration. Additionally, the third suture segment 803c can include a third set of characteristics or features thereby forming a third suture configuration. One or more of the configurations can be the same and/or different. In examples, features or characteristics of each suture segment can include one or more of the following that can be the same or different, length, colors or dyes, filament sizes or characteristics, barb sizes, suture types, materials, needles and their characteristics, and/or the like as described herein.

In one example, the first, second, and third suture segments 802a, 802b, 802c can include a needle or insertion device (not shown) a respective proximal end thereof. The first and second needles or insertion devices (e.g., that can be similar to 101a, 101b) can be any suitable needle or insertion devices configured to pass through tissue. Further, the needles or insertion devices can be made of any suitable material such as steel, Ethalloy, and/or the like, can be any suitable shape and size such as straight, curved, and/or the like, and or may have any other suitable properties including tapered cut, tapered point, blunt tips, and/or the like such that the needles or insertion devices can be inserted and can pass through tissue to enable the first, second, and third suture segments 802a, 802b, 802c to pass through and approximate the tissue as described herein. In an example, the needles or insertion devices can be the same. For example, the needles or insertion devices can be the same material, shape, size, and/or the like (i.e. they can have the same properties as each other). In an additional example, the needles or insertion devices can be different. For example, the needles or insertion devices can be different materials, shapes, sizes, and/or the like (i.e. they can have one or more properties that are different from each other).

As described herein, in one or more examples, the first, second, and third suture segments 802a, 802b, 802c can include a respective distal end. The distal ends thereof can have a fixation tab or stop element as described herein, respectively, attached thereto or formed therefrom. The fixation tabs can be joined together using various methods such as lamination as described herein to form the transition zone 807 (e.g., the connecting section) between the the first, second, and third suture segments 802a, 802b, 802c. As such, in examples herein, the fixation tabs or stop elements can provide an adequate surface area to laminate fixation tab surfaces together using RF energy or other means of joining dissimilar materials together to create the bi-directional strand. Additionally, in an example (e.g., described in FIGS. 8-13B), an additional tab can be used to form the transition zone or connecting section 807. In examples herein, the transition zone or connecting section 807 can be a transition point between one suture segment and another suture segment (e.g., a transition point between two sutures connected together as described herein). Additionally, according to one or more examples, the transition zone or connecting section 807 and each respective fixation tab or stop element can provides a tactile indicator to the user of the wound closure device that each leg may be appropriately seated in tissue. After lamination, in an example, a portion of the connecting section or transition zone 807 can also be trimmed or punched away to reduce the size or change the shape of the transition zone or connecting section.

Various aspects of the wound closure device and subject matter described herein can be set out in the following example sets that can be independent of or in combination with other example sets.

Example Set 1

Example 1—A wound closure device can be provided. The wound closure device comprising: a first suture segment having a first suture configuration; a second suture segment having a second suture configuration, the second suture segment being different than the first suture segment; and a connecting section configured to provide a transition from the first suture segment to the second suture segment.

Example 2—The wound closure device of Example 1, wherein the first suture configuration comprises a first plurality of barbs having a first barb size extending from a first filamentary element having a first filament size.

Example 3—The wound closure device of one or more of Examples 1 and/or 2, wherein the second suture configuration comprises a second plurality of barbs having a second barb size extending from a second filamentary element having a second filament size.

Example 4—The wound closure device of Example 3, wherein the first and second barb sizes are different.

Example 5—The wound closure device of Example 3, wherein the first and second filament sizes are the same.

Example 6—The wound closure device of one or more of Examples 2-5, wherein the first and second filament sizes are different.

Example 7—The wound closure device of one or more of Examples 3-6, wherein the first plurality of barbs have a first shape and the second plurality of barbs have a second shape, wherein the first and second shapes are different.

Example 8—The wound closure device of one or more of Examples 1-7, wherein the first suture segment has a first proximal end and a first distal end, the first distal end having a first stop element integrally formed therefrom, and the second suture segment has a second proximal end and a second distal end, the second distal end having a second stop element integrally formed therefrom, and wherein the connecting section comprising at least a portion of the first stop element laminated to at least a portion of the second stop element.

Example 9—The wound closure device of Example 8, further comprising a third stop element a separate from the first and second suture segments and first and second stop elements, wherein the connecting section comprises at least a portion of the third stop element laminated to at least a portion of the first and second stop elements.

Example 10—The wound closure device of one or more of Examples 3-9, wherein the first plurality of barbs comprise symmetric barbs and the second plurality of barbs comprise spiral barbs.

Example 11—The wound closure device of one or more of Examples 1-10, wherein the first suture segment comprises a first polymer material and the second suture segment comprises a second polymer material.

Example 12—The wound closure device of Example 11, wherein first and second polymer materials are the same.

Example 13—The wound closure device of Example 11, wherein the first and second polymer materials are different.

Example 14—The wound closure device of Example 11, wherein the first and second polymer materials are non-polar materials configured to be plasma treated to create a polar substrate prior to forming the connecting section.

Example 15—The wound closure device of one or more of Examples 1-14, wherein the second suture configuration comprises a second filamentary element having a second filament size.

Example 16—The wound closure device of Example 15, wherein the first and second filament sizes are the same.

Example 17—The wound closure device of Example 15, wherein the first and second filament sizes are different.

Example 18—The wound closure device of Example 15, wherein the second filamentary element comprises a monofilament.

Example 19—The wound closure device of Example 15, wherein the second filamentary element comprises a multi-filament.

Example 20—The wound closure device of one or more of Examples 1-19, wherein the first suture configuration has a first color and the second suture configuration has a second color, and wherein the first and second colors are different from each other.

Example 21—The wound closure device of one or more of Examples 1-20, wherein the first suture segment comprises a first filamentary element having a first length and the second suture segment comprises a second filamentary element having a second length, wherein the first and second lengths are different.

Example Set 2

Example 1—A wound closure device can be provided. The wound closure device comprising: a first suture segment comprising a first filamentary element and a first plurality of barbs extending therefrom, the first suture segment having a first proximal end and a first distal end, the first proximal end having a needle attached thereto and the first distal end having a first stop element integrally formed therefrom, the first suture segment having a first suture configuration; a second suture segment comprising a second filamentary element and a second plurality of barbs extending therefrom, the second suture segment having a second proximal end and a second distal end, the second proximal end having a needle attached thereto and the second distal end having a stop element integrally formed therefrom, the second suture segment having a second suture configuration, the second suture segment being different than the first suture segment; and a connecting section configured to join the first suture segment and the second suture segment, the connecting section comprising at least a portion of the first stop element laminated to at least a portion of the second stop element.

Example 2—The wound closure device of Example 1, further comprising a third stop element a separate from the first and second suture segments and first and second stop elements, wherein the connecting section comprises at least a portion of the third stop element laminated to at least a portion of the first and second stop elements.

Example 3—The wound closure device of one or more of Examples 1 and/or 2, wherein the first suture configuration comprises the first plurality of barbs having a first barb size.

Example 4—The wound closure device of Example 3, wherein the second suture configuration comprises the second plurality of barbs having a second barb size.

Example 5—The wound closure device of one or more of Examples 3 and/or 4, wherein the first and second barb sizes are different.

Example 6—The wound closure device of one or more of Examples 2-5 wherein the first and second filament sizes are the same.

Example 7—The wound closure device of one or more of Examples 2-5, wherein the first and second filament sizes are different.

Example 8—The wound closure device of one or more of Examples 2-7, wherein the first suture configuration comprises the first plurality of barbs being symmetric and the second suture configuration comprises the second plurality of barbs being spiral.

Example 9—The wound closure device of one or more of Examples 1-8, wherein the first suture configuration has a first color and the second suture configuration has a second color, and wherein the first and second colors are different from each other.

Example Set 3

Example 1—A wound closure device, can be provided. The wound closure device comprising: a first suture segment comprising a first filamentary element and a first plurality of barbs, the first suture segment having a first proximal end and a first distal end, the first proximal end having a needle attached thereto and the first distal end having a first stop element integrally formed therefrom; a second suture segment comprising a second filamentary element, the second suture segment having a second proximal end and a second distal end, the second proximal end having a needle attached thereto; a second stop element separate from the first and second suture segments; and a connecting section configured to join the first suture segment and the second suture segment, the connecting section comprising at least a portion of the first stop element laminated to at least a portion of the second stop element with at least a portion second distal end of the suture configuration laminated between the portions of the first and second stop elements.

Example 2—The wound closure device of Example 1, wherein the first suture configuration comprises the first filamentary element having a first filament size and the second suture configuration comprises the second filamentary element having a second filament size.

Example 3—The wound closure device of Example 2, wherein the first and second filament sizes are the same.

Example 4—The wound closure device of Example 2, wherein the first and second filament sizes are different.

Example 5—The wound closure device of one or more of Examples 1-4, wherein the second suture configuration comprises the second filamentary element being a monofilament.

Example 6—The wound closure device of one or more of Examples 1-4, wherein the second suture configuration comprises the second filamentary element being a multifilament.

Example 7—The wound closure device of one or more of Examples 1-6, wherein the first suture configuration has a first color and the second suture configuration has a second color, and wherein the first and second colors are different from each other.

Example Set 3

Example 1—A wound closure device can be provided. The wound closure device comprising: a first suture segment having a first suture configuration; a second suture segment having a second suture configuration, the second suture segment being different than the first suture segment; a third suture segment having a third suture configuration, the third suture segment being different than at least one of the first and second suture segments; and a connecting section configured to provide a transition from the first suture segment to the second suture segment.

Example 2—The wound closure device of Example 1, wherein the first suture configuration comprises a first plurality of barbs having a first barb size extending from a first filamentary element having a first filament size.

Example 3—The wound closure device of one or more of Examples 1 and/or 2, wherein the second suture configuration comprises a second plurality of barbs having a second barb size extending from a second filamentary element having a second filament size.

Example 4—The wound closure device of one or more of Examples 1-3, wherein the third suture configuration comprises a third plurality of barbs having a third barb size extending from a third filamentary element having a third filament size.

Example 5—The wound closure device of Example 4, wherein at least one of the first, second, and third barb sizes are different.

Example 6—The wound closure device of Example 4, wherein the first, second, and third filament sizes are the same.

Example 7—The wound closure device of one or more of Examples 2-6, wherein the first, second, and third filament sizes are different.

Example 8—The wound closure device of one or more of Examples 2-7, wherein the first plurality of barbs have a first shape, the second plurality of barbs have a second shape, and the third plurality of barbs have a third shape, wherein one at least one of the first, second, and third shapes are different.

Example 9—The wound closure device of one or more of Examples 2-8, wherein the first suture segment has a first proximal end and a first distal end, the first distal end having a first stop element integrally formed therefrom, the second suture segment has a second proximal end and a second distal end, the second distal end having a second stop element integrally formed therefrom, and the third suture segment has a third proximal end and a third distal end, the third distal end having a third stop element integrally formed therefrom, and wherein the connecting section comprising at least a portion of the first stop element laminated to at least a portion of the second stop element and at least a portion of the second stop element laminated to at least a portion of the third stop element.

Example 10—The wound closure device of Example 9, further comprising a fourth stop element a separate from the first, second, and third suture segments and first, second, and third stop elements, wherein the connecting section comprises at least a portion of the fourth stop element laminated to at least a portion of at least one of the first and third stop elements.

Example 11—The wound closure device of one or more of Examples 2-10, wherein at least one of the first, second, and third plurality of barbs comprise symmetric barbs and at least one other of the first, second, or third plurality of barbs comprise spiral barbs.

Example 12—The wound closure device of one or more of Examples 1-11, wherein the first suture segment comprises a first polymer material, the second suture segment comprises a second polymer material, and the third suture segment comprises a third polymer material.

Example 13—The wound closure device of Example 12, wherein first, second, and third polymer materials are the same.

Example 14—The wound closure device of Example 12, wherein at least one of the first, second, and third polymer materials is different.

Example 15—The wound closure device of Example 12, wherein at least one of the first, second, and third polymer materials are non-polar materials configured to be plasma treated to create a polar substrate prior to forming the connecting section.

Example 16—The wound closure device of one or more of Examples 1-3, wherein the third suture configuration comprises a third filamentary element having a third filament size.

Example 17—The wound closure device of Example 16, wherein the first, second, and third filament sizes are the same.

Example 18—The wound closure device of Example 16, wherein the at least one of the first, second, and third filament sizes is different.

Example 19—The wound closure device of one or more of Examples 16-18, wherein the third filamentary element comprises a monofilament.

Example 20—The wound closure device of one or more of Examples 16-18, wherein the third filamentary element comprises a multi-filament.

Example 21—The wound closure device of one or more of Examples 1-20, wherein the first suture configuration has a first color, the second suture configuration has a second color, and the third suture configuration has a third color, wherein at least one of the first, second, and third colors is different from the others.

Example 22—The wound closure device of one or more of Examples 1-21, wherein the first suture segment comprises a first filamentary element having a first length, the second suture segment comprises a second filamentary element having a second length, and the third suture segment comprises a third filamentary element having a third length, wherein at least one of the first, second, and third lengths is different from the others.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A wound closure device, the wound closure device comprising:
    a first suture segment having a first suture configuration, the first suture segment having a first proximal end and a first distal end, the first distal end having a first stop element integrally formed therefrom;
    a second suture segment having a second suture configuration that is different than the first suture configuration, the second suture segment having a second proximal end and a second distal end, the second distal end having a second stop element integrally formed therefrom;
    a third suture segment having a third stop element separate from the first and second suture segments and first and second stop elements; and
    a connecting section configured to provide a transition between the first suture segment, the second suture segment and the third suture segment;
    wherein the connecting section comprises at least a portion of the third stop element laminated to at least a portion of the first and second stop elements.

2. The wound closure device of claim 1, wherein the first suture configuration comprises a first plurality of barbs having a first barb size extending from a first filamentary element having a first filament size.

3. The wound closure device of claim 2, wherein the second suture configuration comprises a second plurality of barbs having a second barb size extending from a second filamentary element having a second filament size.

4. The wound closure device of claim 3, wherein the first and second barb sizes are different.

5. The wound closure device of claim 3, wherein the first and second filament sizes are the same.

6. The wound closure device of claim 3, wherein the first and second filament sizes are different.

7. The wound closure device of claim 3, wherein the first plurality of barbs have a first shape and the second plurality of barbs have a second shape, wherein the first and second shapes are different.

8. The wound closure device of claim 3, wherein the first plurality of barbs comprise symmetric barbs and the second plurality of barbs comprise spiral barbs.

9. The wound closure device of claim 3, wherein the first suture segment comprises a first polymer material and the second suture segment comprises a second polymer material.

10. The wound closure device of claim 9, wherein first and second polymer materials are the same.

11. The wound closure device of claim 9, wherein the first and second polymer materials are different.

12. The wound closure device of claim 9, wherein the first and second polymer materials are non-polar materials configured to be plasma treated to create a polar substrate prior to forming the connecting section.

13. The wound closure device of claim 2, wherein the second suture configuration comprises a second filamentary element having a second filament size.

14. The wound closure device of claim 13, wherein the first and second filament sizes are the same.

15. The wound closure device of claim 13, wherein the first and second filament sizes are different.

16. The wound closure device of claim 13, wherein the second filamentary element comprises a monofilament.

17. The wound closure device of claim 13, wherein the second filamentary element comprises a multi-filament.

18. The wound closure device of claim 1, wherein the first suture configuration has a first color and the second suture configuration has a second color, and wherein the first and second colors are different from each other.

19. The wound closure device of claim 1, wherein the first suture segment comprises a first filamentary element having a first length and the second suture segment comprises a second filamentary element having a second length, wherein the first and second lengths are different.

20. A wound closure device, the wound closure device comprising:
a first suture segment comprising a first filamentary element and a first plurality of barbs extending therefrom, the first suture segment having a first proximal end and a first distal end, the first proximal end having a needle attached thereto and the first distal end having a first stop element integrally formed therefrom, the first suture segment having a first suture configuration;
a second suture segment comprising a second filamentary element and a second plurality of barbs extending therefrom, the second suture segment having a second proximal end and a second distal end, the second proximal end having a needle attached thereto and the second distal end having a stop element integrally formed therefrom, the second suture segment having a second suture configuration, the second suture segment being different than the first suture segment;
a third suture segment having a third stop element separate from the first and second suture segments and first and second stop elements; and
a connecting section configured to join the first suture segment; the second suture segment and the third suture segment;
wherein the connecting section comprises at least a portion of the third stop element laminated to at least a portion of the first and second stop elements.

21. The wound closure device of claim 20, wherein the first suture configuration comprises the first plurality of barbs having a first barb size.

22. The wound closure device of claim 21, wherein the second suture configuration comprises the second plurality of barbs having a second barb size.

23. The wound closure device of claim 22, wherein the first and second barb sizes are different.

24. The wound closure device of claim 20, wherein the first suture configuration comprises the first plurality of barbs being symmetric and the second suture configuration comprises the second plurality of barbs being spiral.

25. The wound closure device of claim 20, wherein the first suture configuration has a first color and the second suture configuration has a second color, and wherein the first and second colors are different from each other.

26. The wound closure device of claim 20, wherein the first suture configuration comprises the first filamentary element having a first filament size and the second suture configuration comprises the second filamentary element having a second filament size.

27. The wound closure device of claim 26, wherein the first and second filament sizes are the same.

28. The wound closure device of claim 26, wherein the first and second filament sizes are different.

29. The wound closure device of claim 20, wherein the second suture configuration comprises the second filamentary element being a monofilament.

30. The wound closure device of claim 20, wherein the second suture configuration comprises the second filamentary element being a multi-filament.

31. A wound closure device, the wound closure device comprising:
a first suture segment having a first suture configuration;
a second suture segment having a second suture configuration, the second suture segment being different than the first suture segment;
a third suture segment having a third suture configuration, the third suture segment being different than at least one of the first and second suture segments; and a connecting section configured to provide a transition from the first suture segment to the second suture segment;
wherein the first suture configuration comprises a first plurality of barbs having a first barb size extending from a first filamentary element having a first filament size;
wherein the second suture configuration comprises a second plurality of barbs having a second barb size extending from a second filamentary element having a second filament size;
wherein the third suture configuration comprises a third plurality of barbs having a third barb size extending from a third filamentary element having a third filament size; and
wherein the first suture segment has a first proximal end and a first distal end, the first distal end having a first stop element integrally formed therefrom, the second suture segment has a second proximal end and a second distal end, the second distal end having a second stop element integrally formed therefrom, and the third suture segment has a third proximal end and a third distal end, the third distal end having a third stop element integrally formed therefrom, and wherein the connecting section comprising at least a portion of the first stop element laminated to at least a portion of the second stop element and at least a portion of the second stop element laminated to at least a portion of the third stop element.

32. The wound closure device of claim 31, wherein at least one of the first, second, and third barb sizes are different.

33. The wound closure device of claim 31, wherein the first, second, and third filament sizes are the same.

34. The wound closure device of claim 31, wherein the first, second, and third filament sizes are different.

35. The wound closure device of claim 31, wherein the first plurality of barbs have a first shape, the second plurality of barbs have a second shape, and the third plurality of barbs have a third shape, wherein one at least one of the first, second, and third shapes are different.

36. The wound closure device of claim 31, further comprising a fourth stop element a separate from the first, second, and third suture segments and first, second, and third stop elements, wherein the connecting section comprises at least a portion of the fourth stop element laminated to at least a portion of at least one of the first and third stop elements.

37. The wound closure device of claim 31, wherein at least one of the first, second, and third plurality of barbs comprise symmetric barbs and at least one other of the first, second, or third plurality of barbs comprise spiral barbs.

38. The wound closure device of claim 31, wherein the first suture segment comprises a first polymer material, the second suture segment comprises a second polymer material, and the third suture segment comprises a third polymer material.

39. The wound closure device of claim 38, wherein first, second, and third polymer materials are the same.

40. The wound closure device of claim 38, wherein at least one of the first, second, and third polymer materials is different.

41. The wound closure device of claim 38, wherein at least two of the first, second, and third polymer materials are non-polar materials configured to be plasma treated to create a polar substrate prior to forming the connecting section.

42. The wound closure device of claim 31, wherein the third suture configuration comprises a third filamentary element having a third filament size.

43. The wound closure device of claim 42, wherein the first, second, and third filament sizes are the same.

44. The wound closure device of claim 42, wherein the at least one of the first, second, and third filament sizes is different.

45. The wound closure device of claim 42, wherein the third filamentary element comprises a monofilament.

46. The wound closure device of claim 42, wherein the third filamentary element comprises a multi-filament.

47. The wound closure device of claim 31, wherein the first suture configuration has a first color, the second suture configuration has a second color, and the third suture configuration has a third color, wherein at least one of the first, second, and third colors is different from the others.

48. The wound closure device of claim 31, wherein the first suture segment comprises a first filamentary element having a first length, the second suture segment comprises a second filamentary element having a second length, and the third suture segment comprises a third filamentary element having a third length, wherein at least one of the first, second, and third lengths is different from the others.

* * * * *